United States Patent
Hoelzl et al.

(10) Patent No.: US 9,321,902 B2
(45) Date of Patent: Apr. 26, 2016

(54) ISOINDOLO[2, 1-A]QUINAZOLINE DERIVATIVES FOR STABILIZATION OF ORGANIC MATERIALS

(71) Applicant: BASF SE, Ludwigshafen (DE)

(72) Inventors: Werner Hoelzl, Eschentzwiller (FR); Bruno Rotzinger, Delémont (CH)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/381,387

(22) PCT Filed: Mar. 19, 2013

(86) PCT No.: PCT/EP2013/055713
§ 371 (c)(1),
(2) Date: Aug. 27, 2014

(87) PCT Pub. No.: WO2013/139799
PCT Pub. Date: Sep. 26, 2013

(65) Prior Publication Data
US 2015/0087755 A1 Mar. 26, 2015

Related U.S. Application Data

(60) Provisional application No. 61/612,992, filed on Mar. 20, 2012.

(30) Foreign Application Priority Data

Mar. 20, 2012 (EP) ..................................... 12160265

(51) Int. Cl.
*C07D 487/04* (2006.01)
*C08K 5/101* (2006.01)
(Continued)

(52) U.S. Cl.
CPC ............ *C08K 5/3465* (2013.01); *C07D 401/00* (2013.01); *C07D 403/04* (2013.01); *C07D 487/04* (2013.01); *C08K 5/101* (2013.01); *C08K 5/52* (2013.01); *C09K 15/30* (2013.01)

(58) Field of Classification Search
CPC .............................. C07D 487/04; C08K 5/101
USPC .............................. 544/115, 165, 246; 524/89
See application file for complete search history.

(56) References Cited

U.S. PATENT DOCUMENTS

| 3,509,147 A * | 4/1970 | Houlihan | ............. | C07D 487/04 544/115 |
| 2014/0058021 A1 | 2/2014 | Fischer et al. | | |

FOREIGN PATENT DOCUMENTS

| WO | WO 2012/150527 A1 | 11/2012 |
| WO | WO 2014/009361 A1 | 1/2014 |

OTHER PUBLICATIONS

Kumar et al., A new three-component reaction: Green synthesis of novel Isoindolo[2,1-a]quinazoline derivatives as potent inhibitors of TNF-alpha, Supplementary Material for Chemical Communications , The Royal Society of Chemistry 2011.*

(Continued)

*Primary Examiner* — James J Seidleck
*Assistant Examiner* — Deve E Valdez
(74) *Attorney, Agent, or Firm* — Oblon, McClelland, Maier & Neustadt, L.L.P.

(57) ABSTRACT

The present invention relates to a composition, which comprises a) an organic material susceptible to oxidative, thermal or light-induced degradation, which is a polymer, an oligohydroxy compound, a wax, a fat or a mineral oil, with the proviso that the polymer is not a polypeptide, agar-agar or a component of agar-agar and the oligohydroxy compound is not glucose or a component of agar-agar; and b) a compound of formula (I) n is 1, 2, 3 or 4; when n is 1, $R_5$ is H, $C_1$-$C_{30}$-alkyl, $C_3$-$C_{10}$-cycloalkyl, $C_6$-$C_{10}$-aryl, which is unsubstituted or substituted by $C_1$-$C_8$-alkyl, $C_1$-$C_8$-alkoxy, halogen or one phenyl, $C_7$-$C_{13}$-aralkyl, $C_2$-$C_{22}$-alkenyl, $C_3$-$C_{12}$-alkinyl, OH, $C_1$-$C_{30}$-alkyloxy, $C_3$-$C_{10}$-cycloalkyloxy, $C_6$-$C_{12}$-aryloxy, $C_7$-$C_{13}$-aralkyloxy, hydroxy-$C_1$-$C_8$-alkyl, carboxy-$C_1$-$C_{12}$-alkyl, $C_1$-$C_{12}$-alkoxycarbonyl-$C_1$-$C_{12}$-alkyl, $C_2$-$C_{30}$-alkyl, which is interrupted by one or more oxygen atoms, $C_2$-$C_{16}$-alkyl, which is interrupted by one sulfur atom, or $NR'_1R'_2$; when n is 2, $R_5$ is $C_1$-$C_{12}$-alkane-diyl, $C_6$-$C_{14}$-arylene, $C_4$-$C_8$-cycloalkane-bis-($C_1$-$C_4$-alkylene), $C_6$-$C_{14}$-arene-bis-($C_1$-$C_4$-alkylene), $C_4$-$C_{24}$-alkane-diyl, which is interrupted by one or more oxygen atoms, $C_4$-$C_{20}$-alkane-diyl, which is interrupted by one or more —NH—, —N($C_1$-$C_8$-alkyl)- or —N(hydroxy-$C_1$-$C_8$-alkyl)-, piperazine-N,N'-bis-($C_1$-$C_4$-alkylene) or $C_2$-$C_{10}$-alkane-diyl, which is interrupted by one sulfur atom; $R_1$ to $R_4$ and $R_6$ to $R_9$ are each independently from each other H, $C_1$-$C_{12}$-alkyl, $C_3$-$C_{10}$-cycloalkyl, $C_3$-$C_{22}$-alkenyl, $C_1$-$C_{12}$-alkoxy, $C_1$-$C_{12}$-alkylsulfanyl, hydroxy-$C_1$-$C_8$-alkyl, halogen, $NR''_1R''_2$, $NO_2$, CN, phenyl, phenyloxy or $R_1$ and $R_2$ or $R_2$ and $R_3$ or $R_3$ and $R_4$ or $R_6$ and $R_7$ or $R_7$ and $R_8$ or $R_8$ and $R_9$ are linked together to form a five- or 6-membered alicylic, aromatic or heterocyclic ring together with their 2 corresponding carbons atoms, to which they are attached.

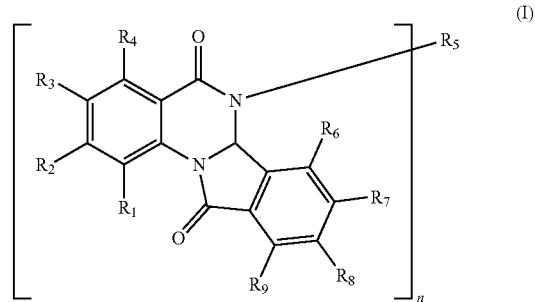

28 Claims, No Drawings

(51) Int. Cl.
  *C08K 5/3465* (2006.01)
  *C09K 15/30* (2006.01)
  *C07D 401/00* (2006.01)
  *C07D 403/04* (2006.01)
  *C08K 5/52* (2006.01)

(56) References Cited

OTHER PUBLICATIONS

U.S. Appl. No. 14/410,979, filed Dec. 23, 2014, Schoening, et al.
International Search Report issued Apr. 12, 2013 in PCT/EP2013/055713.
European Search Report issued Aug. 3, 2012 in Patent Application No. EP 12 16 0265.

K Siva Kumar, et al., "A new three-component reaction: green synthesis of novel isoindolo [2, 1-a]quinazoline derivatives as potent inhibitors of TNF-[alpha]", Chemical Communications, vol. 47, No. 17, The Royal Society of Chemistry, XP 55034591, (Jan. 1, 2011), pp. 5010-5012.

L. Yu Ukhin, et al., "Anthranilic acid hydrazide in the synthesis of fused polycyclic compounds with quinazoline moieties", Russian Chemical Bulletin, vol. 57, No. 11, XP 019753326, (Nov. 2008), pp. 2340-2348.

Nitin T. Patil, et al., "New Linearly and Angularly Fused Quinazolinones: Synthesis through Gold(I)-Catalyzed Cascade Reactions and Anticancer Activities", European Journal of Organic Chemistry, vol. 2012, No. 9, XP 55034660, (Mar. 1, 2012), pp. 1790-1799.

* cited by examiner

ISOINDOLO[2, 1-A]QUINAZOLINE DERIVATIVES FOR STABILIZATION OF ORGANIC MATERIALS

Organic materials are susceptible to degradation, which can be induced by heat, light and/or oxidation. For the reduction of such a degradation, numerous solutions in regard to an incorporation or addition of a stabilizer are proposed.

There is still a need for further technical solutions towards stabilisation of organic material against the detrimental impact of heat, light and/or oxidation.

Annali di Chemica, 64, 1974, pages 421 to 424 discloses the synthesis of 6,6a-dihydro-isoindolo[2,1-a]quinazoline-5,11-dione by condensation of anthranilic acid amide and phthalaldehydic acid. Furthermore, the synthesis of 6-methyl-6,6a-dihydro-isoindolo[2,1-a]quinazoline-5,11-dione by condensation of 2-amino-N-methyl-benzamide and phthalaldehydic acid is disclosed.

Annali di Chemica, 64, 1974, pages 445 to 453 discloses the synthesis of 6-hydroxy-6,6a-dihydro-isoindolo[2,1-a]quinazoline-5,11-dione (CAS-No. 57560-87-9) by condensation of 2-amino-N-hydroxy-benzamide and phthalaldehydic acid.

Russian Chemical Bulletin, International Edition, 2008, Vol. 57, 11, pages 2340 to 2348 discloses the synthesis of 6-amino-6,6a-dihydro-isoindolo[2,1-a]quinazoline-5,11-dione, 6-dimethylamino-6,6a-dihydro-isoindolo[2,1-a]quinazoline-5,11-dione and N-(5,11-dioxo-6a,11-dihydro-5H-isoindolo[2,1-a]quinazolin-6-yl)-acetamide.

Chemical Communications, 2011, 47, pages 5010 to 5012, discloses a three-component reaction, which yields isoindolo[2,1-a]quinazoline-5,11-dione derivatives. Some of these obtained derivatives act as an inhibitor of Tumor Necresis Factor-alpha, which is a key cytokine mediator involved in the inflammatory response.

US-A-2009/0163545 discloses inter alia the protocol of an assay, in which compounds are screened for their ability to alter the lifespan of eukaryontic cells. In the assay, a tested compound gets in contact with an aqueous solution comprising agar-agar, which contains heteropolysaccharids, up to 70% agarose and up to 30% agaropektin, polypeptides like in peptones and glucose. Inter alia, the following specific isoindolo[2,1-a]quinazoline derivatives are reported to have been screened: (S)-6a-6-Phenyl-6,6a-dihydro-isoindolo[2,1-a]quinazoline-5,11-dione (CAS-No. 1164490-21-4), 6-o-Tolyl-6,6a-dihydro-isoindolo[2,1-a]quinazoline-5,11-dione (CAS-No. 375834-34-7), 6-(4-Fluoro-phenyl)-9,10-dimethoxy-6,6a-dihydro-isoindolo[2,1-a]quinazoline-5,11-dione (CAS-No. 375829-57-5), 9,10-Dimethoxy-6-phenyl-6,6a-dihydro-isoindolo[2,1-a]quinazoline-5,11-dione (CAS-No. 374771-80-9), 6-Furan-2-ylmethyl-6,6a-dihydro-isoindolo[2,1-a]quinazoline-5,11-dione (CAS-No. 383149-01-7), 6-(2-Fluoro-phenyl)-6,6a-dihydro-isoindolo[2,1-a]quinazoline-5,11-dione (CAS-No. 374914-81-5) and 6-hydroxy-6,6a-dihydro-isoindolo[2,1-a]quinazoline-5,11-dione (CAS-No. 57560-87-9).

It has now been found that a specific group of isoindolo[2,1-a]quinazoline derivatives is suitable for stabilization of an organic material against degradation by heat, light and/or oxidation.

The present invention relates to a composition, which comprises a) an organic material susceptible to oxidative, thermal or light-induced degradation, which is a polymer, an oligohydroxy compound, a wax, a fat or a mineral oil, with the proviso that the polymer is not a polypeptide, agar-agar or a component of agar-agar and the oligohydroxy compound is not glucose or a component of agar-agar; and b) a compound of formula I

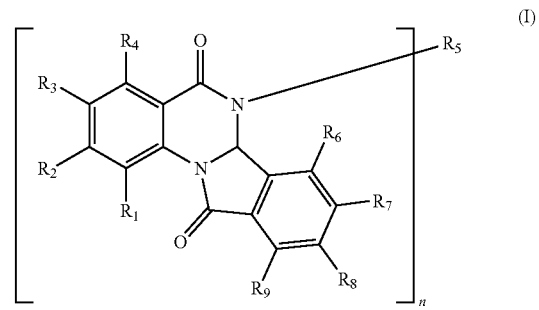

wherein
when n is 1,
$R_5$ is H, $C_1$-$C_{30}$-alkyl, $C_3$-$C_{10}$-cycloalkyl, $C_6$-$C_{10}$-aryl, which is unsubstituted or substituted by $C_1$-$C_8$-alkyl, $C_1$-$C_8$-alkoxy, halogen or one phenyl, $C_7$-$C_{12}$-aralkyl, $C_2$-$C_{22}$-alkenyl, $C_3$-$C_{12}$-alkinyl, OH, $C_1$-$C_{30}$-alkyloxy, $C_3$-$C_{10}$-cycloalkyloxy, $C_6$-$C_{12}$-aryloxy, $C_7$-$C_{12}$-aralkyloxy, hydroxy-$C_1$-$C_8$-alkyl, carboxy-$C_1$-$C_{12}$-alkyl, $C_1$-$C_{12}$-alkoxycarbonyl-$C_1$-$C_{12}$-alkyl, $C_2$-$C_{30}$-alkyl, which is interrupted by one or more oxygen atoms, $C_2$-$C_{16}$-alkyl, which is interrupted by one sulfur atom, or $NR'_1R'_2$;
when n is 2,
$R_5$ is $C_1$-$C_{12}$-alkane-diyl, $C_6$-$C_{14}$-arylene, $C_4$-$C_8$-cycloalkane-bis-($C_1$-$C_4$-alkylene), $C_6$-$C_{14}$-arene-bis-($C_1$-$C_4$-alkylene), $C_4$-$C_{24}$-alkane-diyl, which is interrupted by one or more oxygen atoms, $C_4$-$C_{20}$-alkane-diyl, which is interrupted by one or more —NH—, —N($C_1$-$C_8$-alkyl)- or —N(hydroxy-$C_1$-$C_8$-alkyl)-, piperazine-N,N'-bis-($C_1$-$C_4$-alkylene) or $C_4$-$C_{10}$-alkane-diyl, which is interrupted by one sulfur atom;
when n is 3,
$R_5$ is $C_5$-$C_{12}$-alkane-triyl, $C_5$-$C_{24}$-alkane-triyl, which is interrupted by one or more oxygen atoms, or $C_5$-$C_{24}$-alkane-triyl, which is interrupted by one or more —NH—, —N($C_1$-$C_8$-alkyl)- or —N(hydroxy-$C_1$-$C_8$-alkyl)-;
when n is 4,
$R_5$ is $C_5$-$C_{24}$-alkane-tetrayl, $C_6$-$C_{24}$-alkane-tetrayl, which is interrupted by one or more oxygen atoms, or $C_6$-$C_{24}$-alkane-tetrayl, which is interrupted by one or more —NH—, —N($C_1$-$C_8$-alkyl)- or —N(hydroxy-$C_1$-$C_8$-alkyl)-;
n is 1, 2, 3 or 4;
$R_1$ to $R_4$ and $R_6$ to $R_9$ are each independently from each other H, $C_1$-$C_{12}$-alkyl, $C_3$-$C_{10}$-cycloalkyl, $C_3$-$C_{22}$-alkenyl, $C_1$-$C_{12}$-alkoxy, $C_1$-$C_{12}$-alkylsulfanyl, hydroxy-$C_1$-$C_8$-alkyl, halogen, $NR''_1R''_2$, $NO_2$, CN, phenyl, phenyloxy or $R_1$ and $R_2$ or $R_2$ and $R_3$ or $R_3$ and $R_4$ or $R_6$ and $R_7$ or $R_7$ and $R_8$ or $R_8$ and $R_9$ are linked together to form a five- or 6-membered alicylic, aromatic or heterocyclic ring together with their 2 corresponding carbons atoms, to which they are attached; and
$R'_1$, $R'_2$, $R''_1$ and $R''_2$ are each independently from each other H, $C_1$-$C_{12}$-alkyl, $C_3$-$C_{10}$-cycloalkyl, hydroxy-$C_1$-$C_8$-alkyl, $C_3$-$C_{22}$-alkenyl, $C_6$-$C_{10}$-aryl, which is unsubstituted or substituted by $C_1$-$C_8$-alkyl, $C_1$-$C_8$-alkoxy, halogen or one phenyl, $C_7$-$C_{12}$-aralkyl, carboxy-$C_1$-$C_{12}$-alkyl, $C_1$-$C_{12}$-alkoxycarbonyl-$C_1$-$C_{12}$-alkyl, or carboxy-$C_6$-$C_{10}$-aryl, or $R'_1$ and $R'_2$ or $R''_1$ and $R''_2$ form together with the nitrogen atom, to which they are attached, a 5- or 6-membered alicyclic, aromatic or heterocyclic ring.

A compound of formula I possess at least one asymmetric carbon atom, i.e. the carbon atom at the 6a-position of the isoindolo[2,1-a]quinazoline derivative, which results in enantiomers. The invention relates to any one of these enantiomers or mixtures thereof. Several combinations of substituents at formula I lead to the presence of at least two asymmetric carbon atoms, which results in diastereomers. The invention relates to any one of these diastereomers or mixtures thereof.

$C_1$-$C_{30}$-alkyl is linear or branched and for example methyl, ethyl, n-propyl, 1-methyl-ethyl, n-butyl, 1-methyl-propyl, 2-methyl-propyl, 1,1-dimethyl-ethyl, n-pentyl, 1-methyl-butyl, 3-methyl-butyl, n-hexyl, 1-methyl-pentyl, 2-methyl-pentyl, 4-methyl-pentyl, 2-ethyl-butyl, n-heptyl, 1-methyl-hexyl, n-octyl, 1-methyl-heptyl, 2-ethyl-hexyl, 5,5-dimethyl-hexyl, 1,1,3,3-tetramethyl-butyl, n-nonyl, 2-ethyl-heptyl, n-decyl, undecyl, n-dodecyl, tridecyl, tetradecyl, pentadecyl, n-hexadecyl, n-octadecyl or behenyl. Preferred is $C_1$-$C_{18}$-alkyl, in particular $C_1$-$C_{12}$-alkyl, especially $C_1$-$C_8$-alkyl and very especially $C_1$-$C_4$-alkyl.

$C_3$-$C_{10}$-cycloalkyl is unsubstituted or substituted by $C_1$-$C_4$-alkyl and is for example cyclobutyl, cyclopentyl, 3,4-dimethyl-cyclopentyl, cyclohexyl, 4-methyl-cyclohexyl, 4-(1-methylethyl)-cyclohexyl, 4-(1,1-dimethylethyl)-cyclohexyl, 3,5-dimethyl-cyclohexyl, 5-methyl-2-(1-methylethyl)-cyclohexyl, cycloheptyl or cyclooctyl. Preferred is $C_5$-$C_7$-cycloalkyl, in particular cyclohexyl.

$C_6$-$C_{10}$-aryl, which is unsubstituted or substituted by $C_1$-$C_8$-alkyl, $C_1$-$C_8$-alkoxy, halogen or one phenyl, is for example phenyl, 2-methyl-phenyl, 3-methyl-phenyl, 4-methyl-phenyl, 2,4-dimethyl-phenyl, 3,5-dimethyl-phenyl, 4-(1,1-dimethylethyl)-phenyl, 4-(1,1,3,3-tetramethylpentyl)-phenyl, naphthalen-1-yl, naphthalen-2-yl, 6-methyl-naphthalen-2-yl, 4-phenyl-phenyl, 2-methoxy-phenyl, 3-methoxy-phenyl, 4-methoxy-phenyl, 2-ethoxyphenyl, 3-ethoxy-phenyl, 3-(n-propoxy)-phenyl, 4-(1,1-dimethylethoxy)-phenyl, 2-chloro-phenyl, 3-chlorophenyl, 4-chlorophenyl, 2-chloro-4-methylphenyl. Preferred is $C_6$-$C_{10}$-aryl, which is unsubstituted or substituted by $C_1$-$C_8$-alkyl or $C_1$-$C_8$-alkoxy. Especially preferred is phenyl, which is unsubstituted or substituted by $C_1$-$C_8$-alkyl. Particularly preferred is phenyl.

$C_7$-$C_{13}$-aralkyl is for example benzyl, 4-methyl-benzyl, 2-phenyl-ethyl, 3,5-dimethylbenzyl, 1-phenyl-1,1-dimethyl-methyl, 3-phenyl-propyl, 3-phenyl-2-methyl-propyl, 3,5-di-tert-butyl-benzyl or 4-phenyl-phenyl-methyl. Preferred is benzyl.

$C_2$-$C_{22}$-alkenyl is linear or branched and for example vinyl, allyl, Z- or E-but-2-ene-yl, Z- or E-but-3-ene-yl, Z- or E-pent-2-ene-yl, pent-4-ene-yl, Z- or E-2-methyl-but-2-ene-yl,
Z- or E-3-methyl-but-3-ene-yl, Z- or E-hex-1-ene-yl, Z- or E-hexadec-9-ene-yl or Z- or E-octadec-9-ene-yl, (9Z,12Z)-octadeca-9,12-diene-yl, (9Z,12Z,15Z)-octadeca-9,12,15-triene-yl, (13Z)-docos-13-ene-yl or (13E)-docosene-yl. Preferred is allyl.

$C_3$-$C_{12}$-alkinyl is linear or branched and for example propargyl, but-2-ine-yl or undec-11-ine-yl.

$C_1$-$C_{30}$-alkoxy is linear or branched and for example methoxy, ethoxy, n-propoxy, 1-methyl-ethoxy, n-butoxy, 1-methyl-propoxy, 1,1-dimethyl-ethoxy, n-pentoxy, 2-methyl-pentoxy, 2-ethyl-butoxy, 1-methyl-hexoxy, n-octoxy, 1-methyl-heptoxy, 2-ethyl-hexoxy, 1,1,3,3-tetramethyl-butoxy, 2-ethyl-heptyloxy, n-decyloxy, undecyloxy, n-dodecyloxy, tridecyloxy, tetradecyloxy, pentadecyloxy, n-hexadecyloxy, n-octadecyloxy or behenyloxy. Preferred is $C_1$-$C_{18}$-alkoxy, in particular $C_1$-$C_{12}$-alkoxy, especially $C_1$-$C_8$-alkoxy and very especially $C_1$-$C_4$-alkoxy. Particularly preferred is methoxy and n-propoxy.

$C_3$-$C_{10}$-cycloalkyloxy is unsubstituted or substituted by $C_1$-$C_4$-alkyl and for example cyclopropyloxy, cyclobutyloxy, cyclopentyloxy, 3,4-dimethyl-cyclopentyloxy, cyclohexyloxy, 4-methyl-cyclohexyloxy, 4-(1,1-dimethylethyl)-cyclohexyloxy, 3,5-dimethyl-cyclohexyloxy, cycloheptyloxy or cyclooctyloxy. Preferred is $C_5$-$C_7$-cycloalkyloxy, in particular cyclohexyloxy.

$C_6$-$C_{12}$-aryloxy is unsubstituted or substituted by $C_1$-$C_4$-alkyl and for example phenoxy, 2-methyl-phenoxy, 3-methyl-phenoxy, 4-methyl-phenoxy, 2,4-dimethyl-phenoxy, 3,5-dimethyl-phenoxy, 4-(1,1-dimethylethyl)-phenoxy, 4-(1,1,3,3-tetramethylpentyl)phenoxy or 4-phenyl-phenoxy. Preferred is phenoxy. $C_7$-$C_{13}$-aralkyloxy is unsubstituted or substituted by $C_1$-$C_4$-alkyl and for example benzyloxy, 4-methyl-benzyloxy, 2-phenyl-ethyloxy, 3,5-dimethylbenzyloxy, 1-phenyl-1,1-dimethyl-methyloxy, 3-phenyl-propyloxy, 3,5-di-tert-butyl-benzyl or 4-phenyl-phenyl-methyl. Preferred is benzyloxy.

Hydroxy-$C_1$-$C_8$-alkyl is linear or branched and for example hydroxymethyl, 1-hydroxyethyl, 2-hydroxyethyl, 1-hydroxy-1-methylethyl, 2-hydroxy-1-methylethyl, 3-hydroxy-propyl, 2-hydroxy-butyl, 4-hydroxy-butyl, 2-hydroxy-2-methyl-butyl or 2,3-dihydroxy-propyl. Preferred is 2-hydroxyethyl or 2-hydroxy-1-methyl-ethyl.

Carboxy-$C_1$-$C_{12}$-alkyl is linear or branched and for example carboxymethyl, 2-carboxyethyl, 2-carboxy-2-methylethyl, 3-carboxypropyl, 4-carboxybutyl or 5-carboxypentyl. Preferred is carboxymethyl or 2-carboxyethyl.

$C_1$-$C_{12}$-alkoxy-carbonyl-$C_1$-$C_{12}$-alkyl is linear or branched and for example methoxy-carbonyl-methyl, ethoxy-carbonyl-methyl, 2-(ethoxy-carbonyl)-ethyl, 2-(methoxy-carbonyl)-2-methylethyl, 2-(1,1-dimethylethoxy-carbonyl)-2-methylethyl or 2-ethylhexyl-cabonyl-ethyl. Preferred is 2-(ethoxy-carbonyl)-ethyl.

$C_2$-$C_{30}$-alkyl, which is interrupted by one or more oxygen atoms, is linear or branched and for example methoxy-methyl, 2-methoxy-ethyl, 2-ethoxy-ethyl, 2-(2-methoxy-ethoxy)-ethyl, 2-n-butoxy-ethyl, 2-[2-(2-methoxy-ethoxy)-ethoxy]-ethyl, 2-[2-[2-(2-methoxy-ethoxy)-ethoxy]-ethoxy]-ethyl, 2-(2-methoxy-1-methyl-ethoxy)-1-methyl-ethyl, 3-(n-propoxy)-propyl, 2-[2-[2-(2-n-butoxy-ethoxy)-ethoxy]-ethoxy]-ethyl, 2-[2-(2-n-butoxy-2-methyl-ethoxy)-2-methyl-ethoxy]-2-methyl-ethyl or 2-[(2-n-lauryl)-ethoxy]-ethyl. Preferred is 2-methoxy-ethyl or 2-ethoxy-ethyl.

$C_2$-$C_{16}$-alkyl, which is interrupted by one sulfur atom, is linear or branched and for example 2-(methyl-sulfanyl)-ethyl, 3-thiaundecyl or 3-thiapentadecyl.

Halogen is for example a chlorine atom, a bromine atom or a iodine atom. Preferred is a chlorine atom.

$C_1$-$C_{12}$-alkane-diyl is linear or branched and for example ethylene, 1-methyl-ethane-1,2-diyl, n-propylene, n-butylene, 2-methyl-butane-1,4-diyl, hexamethylene or decane-1,10-diyl.

$C_4$-$C_8$-cycloalkylene is for example cyclopentane-1,2-diyl, cyclopentane-1,3-diyl, cyclohexane-1,4-diyl, cyclohexane-1,2-diyl, cyclooctane-1,2-diyl or cycloheptane-1,3-diyl.

$C_6$-$C_{14}$-arylene is for example 1,3-phenylene, 1,4-phenylene, 2,3-dimethyl-benzene-1,4-diyl, biphenyl-4,4'-diyl, naphthalene-2,6-diyl or naphthalene-1,4-diyl.

$C_4$-$C_8$-cycloalkane-bis-($C_1$-$C_4$-alkylene) is for example cyclopentane-1,3-bismethylene, cyclohexane-1,4-bismethylene, cyclohexane-1,3-bismethylene, cyclohexane-1,4-bisethylene or cyclohexane-1,4-bis(1-methyl-ethane-1,2-diyl).

$C_6$-$C_{14}$-arene-bis-($C_1$-$C_4$-alkylene) is linear or branched and for example benzene-1,3-bismethylene, benzene-1,4-bismethylene, napthaline-1,4-bismethylene, napthaline-2,6-bismethylene, 5-methyl-benzene-1,3-bismethylene, 5-tert-butyl-benzene-1,3-bismethylene, benzene-1,4-bisethylene, benzene-1,4-bis-(1-methyl-ethan-1,2-diyl) or biphenyl-4,4'-bismethylene.

$C_4$-$C_{24}$-alkane-diyl, which is interrupted by one or more oxygen atoms, is linear or branched and for example ethoxy-ethane-2',1-diyl, —($CH_2CH_2$—O)$_2$—$CH_2CH_2$—, —($CH_2CH_2$—O)$_3$—$CH_2CH_2$—, —$CH(CH_3)CH_2$—O—$CH(CH_3)CH_2$—, —[$CH(CH_3)CH_2$—O]$_2$—$CH(CH_3)CH_2$—, —$CH_2CH_2CH_2CH_2$—O—$CH_2CH_2CH_2CH_2$— or —($CH_2CH_2CH_2CH_2$—O)$_2$—$CH_2CH_2CH_2CH_2$—. Preferred is ethoxy-ethane-2',1-diyl or —($CH_2CH_2$—O)$_2$—$CH_2CH_2$—.

$C_4$-$C_{20}$-alkane-diyl, which is interrupted by one or more —NH—, —N($C_1$-$C_8$-alkyl)- or —N(hydroxy-$C_1$-$C_8$-alkyl)-, is linear or branched and for example 3-aza-pentane-1,5-diyl, 4-azaheptane-1,7-diyl, —$CH_2CH_2$—NH—$CH_2CH_2$—NH—$CH_2CH_2$—, —$CH_2$—C($CH_3$)H—NH—$CH_2$—$CH_2$—NH—C($CH_3$)H—$CH_2$—, —$CH_2CH_2$—NH—$CH_2CH_2CH_2$—NH—$CH_2CH_2$—, —$CH_2$—$CH_2$—$CH_2$—NH—$CH_2$—$CH_2$—NH—$CH_2$—$CH_2$—NH—$CH_2$—$CH_2$—, 3-methyl-3-azapentane-1,5-diyl, 3-ethyl-3-azahexane-1,6-diyl, 5-(2-hydroxyethyl)-5-azanonane-1,9-diyl, 4-(2-hydroxyethyl)-4-azaheptane or 5,8-dimethyl-5,8-diazadodecane-1,12-diyl.

Piperazine-N,N'-bis-($C_1$-$C_4$-alkylene) is linear or branched and for example 2-[4-(2-amino-ethyl)piperazine-1-yl]-ethanamine-1,2''-diyl.

$C_2$-$C_{10}$-alkane-diyl, which is interrupted by one sulfur atom, is linear or branched and for example is for example thio-bismethylene, 2-(methylsulfanyl)-ethyl-1,1'-diyl, 2-(ethylsulfanyl)-ethyl-1,2'-diyl, 3-(propylsulfanyl)-propyl-1,3'-diyl, —$CH(CH_3)CH_2$—S—$CH(CH_3)$—$CH_2$— or —$CH(CH_3)CH_2$—S—$CH_2$—$CH(CH_3)$—.

$C_5$-$C_{12}$-alkane-triyl is linear or branched and for example 2,2-dimethyl-propane-1,3,1'-triyl, 3-(ethyl)-pentane-1,5,2'-triyl or 4-methyl-4-(propyl)-heptane-1,7,3'-triyl.

$C_4$-$C_{24}$-alkane-triyl, which is interrupted by one or more —NH—, —N($C_1$-$C_8$-alkyl)- or —N(hydroxy-$C_1$-$C_8$-alkyl), is linear or branched and for example 3-ethyl-3-azapentane-1,5,2'-triyl or 4-propyl-4-azaheptane-1,7,3'-triyl.

$C_5$-$C_{24}$-alkane-tetrayl is linear or branched and for example 2,2-dimethyl-propane-1,3,1',1''-tetrayl, 3,3-diethyl-pentane-1,5,2',2''-tetrayl or 4,4-dipropyl-heptane-1,7,3',3''-tetrayl.

$C_1$-$C_{12}$-alkylsulfanyl is linear or branched and for example methysulfanyl, ethylsulfanyl, n-butylsulfanyl, 1,1-dimethyl-ethylsulfanyl, n-octylsulfanyl or n-dodecylsulfanyl.

A five- or 6-membered heterocyclic ring is for example is for example pyrrolidine, piperidine, azepane, morpholine or 2,6-dimethyl-morpholine.

If reference is made in this description to an organic material susceptible to oxidative, thermal or light-induced degradation, then it is understood that this organic material is a polymer, an oligohydroxy compound, a wax, a fat or a mineral oil, with the proviso that the polymer is not a polypeptide, agar-agar or a component of agar-agar and the oligohydroxy compound is not glucose or a component of agar-agar A polymer is defined herein according to the Organization for Economic Co-operation and Development and is a substance consisting of molecules characterized by the sequence of one or more types of monomer units and comprising a simple weight majority of molecules containing at least three monomer units which are covalently bound to at least one other monomer unit or other reactant and consists of less than a simple weight majority of molecules of the same molecular weight. Such molecules must be distributed over a range of molecular weights wherein differences in the molecular weight are primarily attributable to differences in the number of monomer units. In the context of this definition a monomer unit means the reacted form of a monomer in a polymer.

A polypeptide is a specific polymer, which is obtainable by the polycondensation of α-aminoacids of the general formula $H_2N$—CH(substituent)-COOH or copolymers thereof, wherein the content of the condensed α-aminoacids in the polymer is at least 50% of the weight of the polymer.

Agar-agar is a natural product from the cell wall of algae. It is a mixture comprising gelling agarose (up to 70% by weight) and non-gelling agaropektin (up to 30% by weight). Agarose (CAS-No. 9012-36-6) is a linear polysaccharide out of D-galactose and 3,6-anhydro-L-galactose, which are alternating β-1->4 and α-1->3 glycosidically linked. Agaropektin is a linear polysaccharide mainly out of D-galactose, which is β-1->3 glycosidically linked, wherein some 0-positions are partially esterified with sulphuric acid and wherein some 3,6-anhydro-L-galactose and uronic acids units are also contained.

A polymer can be natural, semi-synthetic or synthetic. A natural polymer is isolated from a natural source without further synthetic modifications. A synthetic polymer does not contain a polymer part isolated from a natural source. A semi-synthetic polymer contains at least one natural polymer part, wherein the natural polymer part can be synthetically modified and/or reacted with monomers to form the semi-synthetic polymer.

A polymer can be thermoplastic, i.e. it can be shaped into a new form at an elevated temperature, for example at a temperature in the range from 135° C. to 350° C., especially from 150° C. to 340° C.

Copolymers are polymers, wherein a further co-monomer is co-polymerized. Preferred are copolymers, wherein the weight content of one or more further co-monomers is below 50%.

Examples of a polymer are:

1. Polymers of monoolefins and diolefins, for example polypropylene, polyisobutylene, polybut-1-ene, poly-4-methylpent-1-ene, polyvinylcyclohexane, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultra-high molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is generated in-situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

A special copolymer of two monoolefins is a pipe grade polypropylene random copolymer, which is obtainable from the polymerization of more than 90% by weight of propylene and of less than 10% by weight, typically between 2 and 6% by weight, of ethylene.

4. Hydrocarbon resins (for example $C_5$-$C_9$) including hydrogenated modifications thereof (e.g. tackifiers) and mixtures of polyalkylenes and starch.

Homopolymers and copolymers from 1.)-4.) may have any stereostructure including syndiotactic, isotactic, hemi-isotactic or atactic; where atactic polymers are preferred. Stereoblock polymers are also included.

5. Polystyrene, poly(p-methylstyrene), poly(α-methylstyrene).

6. Aromatic homopolymers and copolymers derived from vinyl aromatic monomers including styrene, α-methylstyrene, all isomers of vinyl toluene, especially p-vinyl-toluene, all isomers of ethyl styrene, propyl styrene, vinyl biphenyl, vinyl naphthalene, and vinyl anthracene, and mixtures thereof. Homopolymers and copolymers may have any stereostructure including syndiotactic, isotactic, hemi-isotactic or atactic; where atactic polymers are preferred. Stereoblock polymers are also included.

6a. Copolymers including aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof, for example styrene/butadiene, styrene/acrylonitrile, styrene/ethylene (interpolymers), styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

6b. Hydrogenated aromatic polymers derived from hydrogenation of polymers mentioned under 6.), especially including polycyclohexylethylene (PCHE) prepared by hydrogenating atactic polystyrene, often referred to as polyvinylcyclohexane (PVCH).

6c. Hydrogenated aromatic polymers derived from hydrogenation of polymers mentioned under 6a.).

Homopolymers and copolymers may have any stereostructure including syndiotactic, isotactic, hemi-isotactic or atactic; where atactic polymers are preferred. Stereoblock polymers are also included.

7. Graft copolymers of vinyl aromatic monomers such as styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrite/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes, for example polyurethanes synthesized from a polyol and an aliphatic or aromatic polyisocyanate such as polyurethanes derived from hydroxylterminated polyethers, polyesters or polybutadienes on the one hand and aliphatic or aromatic polyisocyanates on the other, as well as precursors thereof.

Hydroxyl-terminated polyethers are known and are prepared, for example, by polymerizing epoxides such as ethylene oxide, propylene oxide, butylene oxide, tetrahydrofuran, styrene oxide or epichlorohydrin with themselves, for example in the presence of $BF_3$, or by addition reaction of these epoxides, alone or as a mixture or in succession, with starting components containing reactive hydrogen atoms, such as water, alcohols, ammonia or amines, for example ethylene glycol, propylene 1,3- and 1,2-glycol, trimethylolpropane, 4,4'-dihydroxydiphenylpropane, aniline, ethanolamine or ethylenediamine. Sucrose polyethers are also suitable in accordance with the invention. In many cases preference is given to those polyethers which predominantly (up to 90% by weight, based on all the OH groups present in the polyether) contain primary OH groups. Furthermore, polyethers modified by vinyl polymers, as are formed, for example, by polymerizing styrene and acrylonitrile in the presence of polyethers, are suitable, as are polybutadienes containing OH groups.

In particular, a polyol compound has a molecular weight of 400-10000, especially 800 to 10000, and is a polyhydroxy compound, especially containing from 2 to 8 hydroxyl groups, especially from 2 to 4.

Suitable polyisocyanates are aliphatic or aromatic, for example ethylene diisocyanate, 1,4-tetramethylene diisocyanate, 1,6-hexamethylene diisocyanate, 1,12-dodecane diisocyanate, cyclobutane 1,3-diisocyanate, cyclohexane 1,3- and -1,4-diisocyanate and also any desired mixtures of these isomers, 1-isocyanato-3,3,5-trimethyl-5-isocyanatomethylcyclohexane, 2,4- and 2,6-hexahydrotolylene diisocyanate and also any desired mixtures of these isomers, hexahydro-1,3- and/or -1,4-phenylene diisocyanate, perhydro-2,4'- and/or -4,4'-diphenylmethanediisocyanate, 1,3- and 1,4-phenylene diisocyanate, 2,4- and 2,6-tolylene diisocyanate, and also any desired mixtures of these isomers, diphenylmethane 2,4'- and/or -4,4'-diisocyanate, naphthylene 1,5-diisocyanate, triphenylmethane 4,4',4"-triisocyanate, polyphenyl-polymethylene polyisocyanates as are obtained by aniline-formaldehyde condensation followed by phosgenization, m- and p-isocyanatophenylsulfonyl isocyanates, perchlorinated aryl polyisocyanates, polyisocyanates containing carbodiimide groups, polyisocyanates containing allophanate groups, polyisocyanates containing isocyanurate groups, polyisocyanates containing urethane groups, polyisocyanates containing acylated urea groups, polyisocyanates containing biuret groups, polyisocyanates containing ester groups, reaction products of the abovementioned isocyanates with acetals, and polyisocyanates containing polymeric fatty acid radicals.

It is also possible to employ the isocyanate group-containing distillation residues, as they are or dissolved in one or more of the abovementioned polyisocyanates, which are obtained in the course of the industrial preparation of isocyanates. It is additionally possible to use any desired mixtures of the abovementioned polyisocyanates.

Preferred are 2,4- or 2,6-tolylene diisocyanate and any desired mixtures of these isomers ("TDI"), polyphenyl-polymethylene-polyisocyanates as prepared by aniline-formaldehyde condensation followed by phosgenization ("crude MDI") or polyisocyanates containing carbodiimide, urethane, allophanate, isocyanurate, urea or biuret groups ("modified polyisocyanates").

The polyurethanes can be homogeneous polyurethanes or cellular.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimides, polyesterimides, polyhydantoins and polybenzimidazoles.

18. Polyesters derived from dicarboxylic acids and diols and/or from hydroxycarboxylic acids or the corresponding lactones or lactides, for example polyethylene terephthalate, polybutylene terephthalate, poly-1,4-dimethylolcyclohexane terephthalate, polyalkylene naphthalate and polyhydroxybenzoates as well as copolyether esters derived from hydroxyl-terminated polyethers, and also polyesters modified with polycarbonates or MBS. Copolyesters may comprise, for example—but are not limited to—polybutylenesuccinate/terephtalate, polybutyleneadipate/terephthalate, polytetramethyleneadipate/terephthalate, polybutylensuccinate/adipate, polybutylensuccinate/carbonate, poly-3-hydroxybutyrate/octanoate copolymer, poly-3-hydroxybutyrate/hexanoate/decanoate terpolymer. Furthermore, aliphatic polyesters may comprise, for example—but are not limited to—the class of poly(hydroxyalkanoates), in particular, poly(propiolactone), poly(butyrolactone), poly(pivalolactone), poly(valerolactone) and poly(caprolactone), polyethylenesuccinate, polypropylenesuccinate, polybutylenesuccinate, polyhexamethylenesuccinate, polyethyleneadipate, polypropyleneadipate, polybutyleneadipate, polyhexamethyleneadipate, polyethyleneoxalate, polypropyleneoxalate, polybutyleneoxalate, polyhexamethyleneoxalate, polyethylenesebacate, polypropylenesebacate, polybutylenesebacate and polylactic acid (PLA) as well as corresponding polyesters modified with polycarbonates or MBS. The term "polylactic acid (PLA)" designates a homopolymer of preferably poly-L-lactide and any of its blends or alloys with other polymers; a co-polymer of lactic acid or lactide with other monomers, such as hydroxy-carboxylic acids, like for example glycolic acid, 3-hydroxy-butyric acid, 4-hydroxy-butyric acid, 4-hydroxy-valeric acid, 5-hydroxyvaleric acid, 6-hydroxy-caproic acid and cyclic forms thereof; the terms "lactic acid" or "lactide" include L-lactic acid, D-lactic acid, mixtures and dimers thereof, i.e. L-lactide, D-lactide, meso-lactide and any mixtures thereof.

19. Polycarbonates and polyester carbonates.

20. Polyketones.

21. Polysulfones, polyether sulfones and polyether ketones.

22. Crosslinked polymers derived from aldehydes on the one hand and phenols, ureas and melamines on the other hand, such as phenol/formaldehyde resins, urea/formaldehyde resins and melamine/formaldehyde resins.

23. Drying and non-drying alkyd resins.

24. Unsaturated polyester resins derived from copolyesters of saturated and unsaturated dicarboxylic acids with polyhydric alcohols and vinyl compounds as crosslinking agents, and also halogen-containing modifications thereof of low flammability.

25. Crosslinkable acrylic resins derived from substituted acrylates, for example epoxy acrylates, urethane acrylates or polyester acrylates.

26. Alkyd resins, polyester resins and acrylate resins crosslinked with melamine resins, urea resins, isocyanates, isocyanurates, polyisocyanates or epoxy resins.

27. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

28. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

29. Blends of the aforementioned polymers (polyblends), for example PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

30. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

31. Aqueous emulsions of natural or synthetic rubber, e.g. natural latex or latices of carboxylated styrene/butadiene copolymers.

An oligohydroxy compound possesses two or more hydroxy groups, but is not a polymer according to the definition for polymers of the Organization for Economic Cooperation and Development. Examples for oligohydroxy compounds are ethylene glycol, propylene glycol, butane-1,2-diol, butane-1,4-diol, hexane-1,2-diol, hexane-1,6-diol, cyclohexane-1,2-diol, glycerol, pentaerythritol, D-fructose, D-glucitol, mannitol or saccharose.

A wax is for example an ester of wax acids with alcohols, for example $C_{22}$-$C_{34}$-monocarboxylic acids esterified with $C_{15}$-$C_{36}$-monoalcohols, triterpene alcohols or steriod alcohol. Such esters are for example contained in carnauba wax, beeswax or jojo-baoil. A further type of wax is for example a Fischer-Tropsch-wax, which is based on $C_1$-chemistry.

A fat is an ester of glycerol and an aliphatic saturated or unsaturated carboxylic acid, for example a monoacyl glycerol, a diacyl glycerol or a triacyl glycerol. Preferably, the carboxylic acid is linear.

A mineral oil is an aliphatic liquid saturated hydrocarbon, which is obtained by destillation from crude oil, coal tar, bituminous tar, wood or peat. The mineral oil can be liquid, semi-solid or solid. In the latter case, it is called mineral fat. Examples for mineral oils are benzine, diesel oil, fuel oil, bitumen or kerosine. Preferred mineral oils are saturated $C_8$-$C_{22}$-hydrocarbons, which are linear or branched. Especially preferred are saturated $C_8$-$C_{14}$-hydrocarbons.

Preferred is a composition which comprises as component a) an organic material susceptible to oxidative, thermal or light-induced degradation, wherein the organic material is a polymer, which is synthetic or semisynthetic, an oligohydroxy compound, a wax, a fat or a mineral oil, and as component b) a compound of formula I.

Preferred is a composition, which comprises an organic material susceptible to oxidative, thermal or light-induced degradation and a compound of formula I, wherein the organic material is a polymer, which is thermoplastic and synthetic or semisynthetic, an oligohydroxy compound, a wax, a fat or a mineral oil.

Preferred is a composition, which comprises an organic material susceptible to oxidative, thermal or light-induced degradation and a compound of formula I, wherein the organic material is a polymer, which is synthetic or semisynthetic.

Preferred is a composition, which comprises an organic material susceptible to oxidative, thermal or light-induced degradation and a compound of formula I, wherein the organic material is a polymer, which is thermoplastic and synthetic or semisynthetic.

Preferred is a composition, which comprises an organic material susceptible to oxidative, thermal or light-induced degradation and a compound of formula I, wherein the organic material is a polyolefin or a copolymer thereof, a polystyrene or a copolymer thereof, a polyurethane or a copolymer thereof, a polyether, which is obtainable by the polycondensation of an expoxide, an oxetane or tetrahydrofuran, or a copolymer thereof, a polyol, a polyester or a copolymer thereof, a polycarbonate or a copolymer thereof, a polyvinyl chloride or a copolymer thereof, a polyvinylidene chloride or a copolymer thereof, a polysulfone or a copolymer thereof, a polybutadiene or a copolymer thereof, a polyvinylacetate or a copolymer thereof, a polyvinylalcohol or a copolymer thereof, polyvinylacetale or a copolymer thereof, a polyamide, which is obtainable by polycondensation of a diamine and a dicarboxylic acid, or a copolymer thereof, a polyamide, which is obtainable by polycondensation of $H_2N$—$(CH_2)_x$—$CH_2$—COOH with x=1 to 10, or a copolymer thereof, an oligohydroxy compound, a wax, a fat or a mineral oil.

Preferred is a composition, which comprises an organic material susceptible to oxidetive, thermal or light-induced degradation and a compound of formula I, wherein the organic material is a polyolefin or a copolymer thereof, a polystyrene or a copolymer thereof, a polyurethane or a copolymer thereof, a polyether, which is obtainable by the polycondensation of an expoxide, an oxetane or tetrahydrofuran, or a copolymer thereof, a polyol, a polyester or a copolymer thereof, a polycarbonate or a copolymer thereof, a polyvinyl chloride or a copolymer thereof, a polyvinylidene chloride or a copolymer thereof, a polysulfone or a copolymer thereof, a polybutadiene or a copolymer thereof, a polyvinylacetate or a copolymer thereof, a polyvinylalcohol or a copolymer thereof, polyvinylacetale or a copolymer thereof or a polyamide, which is obtainable by polycondensation of a diamine and a dicarboxylic acid, or a copolymer thereof, a polyamide, which is obtainable by polycondensation of $H_2N-(CH_2)_x-CH_2-COOH$ with $x=1$ to 10.

Preferred is a composition, which comprises an organic material susceptible to oxidative, thermal or light-induced degradation and a compound of formula I, wherein the organic material is a polyolefin or a copolymer thereof, a polystyrene or a copolymer thereof, a polyurethane or a copolymer thereof or a polyol.

Preferred is a composition, which comprises an organic material susceptible to oxidative, thermal or light-induced degradation and a compound of formula I, wherein the organic material is a polyolefin or a copolymer thereof, a polystryrene or a copolymer thereof or a polyurethane or a copolymer thereof.

Preferred is a composition, which comprises an organic material susceptible to oxidative, thermal or light-induced degradation and a compound of formula I, wherein the organic material is a polyolefin or a copolymer thereof or a polystyrene or a copolymer thereof.

For compositions and preferences thereof as described in this description, a very preferred organic material susceptible to oxidative, thermal or light-induced degradation is a polyolefin or a copolymer thereof.

Preferred is a composition comprising an organic material susceptible to oxidative, thermal or light-induced degradation, i.e. component a), and a compound of formula I, wherein at formula I
when n is 1,
$R_5$ is H, $C_1$-$C_{30}$-alkyl, $C_3$-$C_{10}$-cycloalkyl, $C_6$-$C_{10}$-aryl, which is unsubstituted or substituted by $C_1$-$C_8$-alkyl, $C_1$-$C_8$-alkoxy, halogen or one phenyl, $C_7$-$C_{13}$-aralkyl, $C_2$-$C_{22}$-alkenyl, $C_3$-$C_{12}$-alkinyl, OH, $C_1$-$C_{30}$-alkyloxy, $C_3$-$C_{10}$-cycloalkyloxy, $C_6$-$C_{12}$-aryloxy, $C_7$-$C_{13}$-aralkyloxy, hydroxy-$C_1$-$C_8$-alkyl, carboxy-$C_1$-$C_{12}$-alkyl, $C_1$-$C_{12}$-alkoxycarbonyl-$C_1$-$C_{12}$-alkyl, $C_2$-$C_{30}$-alkyl, which is interrupted by one or more oxygen atoms, $C_2$-$C_{16}$-alkyl, which is interrupted by one sulfur atom, or $NR'_1R'_2$;
when n is 2,
$R_5$ is $C_1$-$C_{12}$-alkane-diyl, $C_6$-$C_{14}$-arylene, $C_4$-$C_8$-cycloalkane-bis-($C_1$-$C_4$-alkylene), $C_6$-$C_{14}$-arene-bis-($C_1$-$C_4$-alkylene), $C_4$-$C_{24}$-alkane-diyl, which is interrupted by one or more oxygen atoms, $C_4$-$C_{20}$-alkane-diyl, which is interrupted by one or more —NH—, —N($C_1$-$C_8$-alkyl)- or —N(hydroxy-$C_1$-$C_8$-alkyl)-, piperazine-N,N'-bis-($C_1$-$C_4$-alkylene) or $C_2$-$C_{10}$-alkane-diyl, which is interrupted by one sulfur atom;
n is 1 or 2;
$R_1$ to $R_4$ and $R_6$ to $R_9$ are each independently from each other H, $C_1$-$C_{12}$-alkyl, $C_3$-$C_{10}$-cycloalkyl, $C_3$-$C_{22}$-alkenyl, $C_1$-$C_{12}$-alkoxy, $C_1$-$C_{12}$-alkylsulfanyl, hydroxy-$C_1$-$C_8$-alkyl, halogen, $NR''_1R''_2$, $NO_2$, CN, phenyl, phenyloxy or $R_1$ and $R_2$ or $R_2$ and $R_3$ or $R_3$ and $R_4$ or $R_6$ and $R_7$ or $R_7$ and $R_8$ or $R_8$ and $R_9$ are linked together to form a five- or 6-membered alicylic, aromatic or heterocyclic ring together with their 2 corresponding carbons atoms; and
$R'_1$, $R'_2$, $R''_1$ and $R''_2$ are each independently from each other H, $C_1$-$C_{12}$-alkyl, $C_3$-$C_{10}$-cycloalkyl, hydroxy-$C_1$-$C_8$-alkyl, $C_3$-$C_{22}$-alkenyl, $C_6$-$C_{10}$-aryl, which is unsubstituted or substituted by $C_1$-$C_8$-alkyl, $C_1$-$C_8$-alkoxy, halogen or one phenyl, $C_7$-$C_{12}$-aralkyl, carboxy-$C_1$-$C_{12}$-alkyl, $C_1$-$C_{12}$-alkoxycarbonyl-$C_1$-$C_{12}$-alkyl, or carboxy-$C_6$-$C_{10}$-aryl, or $R'_1$ and $R'_2$ or $R''_1$ and $R''_2$ form together with the nitrogen atom, to which they are attached, a 5- or 6-membered alicyclic, aromatic or heterocyclic ring.

Preferred is a composition, which comprises an organic material susceptible to oxidative, thermal or light-induced degradation and a compound of formula I, wherein at formula I
when n is 1,
$R_5$ is H, $C_1$-$C_{30}$-alkyl, $C_3$-$C_{10}$-cycloalkyl, $C_6$-$C_{10}$-aryl, which is unsubstituted or substituted by $C_1$-$C_8$-alkyl, $C_1$-$C_8$-alkoxy, halogen or one phenyl, $C_7$-$C_{13}$-aralkyl, $C_2$-$C_{22}$-alkenyl, $C_3$-$C_{12}$-alkinyl, OH, $C_1$-$C_{30}$-alkyloxy, $C_3$-$C_{10}$-cycloalkyloxy, $C_6$-$C_{12}$-aryloxy, $C_7$-$C_{13}$-aralkyloxy, hydroxy-$C_1$-$C_8$-alkyl, carboxy-$C_1$-$C_{12}$-alkyl, $C_1$-$C_{12}$-alkoxycarbonyl-$C_1$-$C_{12}$-alkyl, $C_2$-$C_{30}$-alkyl, which is interrupted by one or more oxygen atoms, $C_2$-$C_{16}$-alkyl, which is interrupted by one sulfur atom, or $NR'_1R'_2$;
when n is 2,
$R_5$ is $C_1$-$C_{12}$-alkane-diyl, $C_6$-$C_{14}$-arylene, $C_4$-$C_8$-cycloalkane-bis-($C_1$-$C_4$-alkylene), $C_6$-$C_{14}$-arene-bis-($C_1$-$C_4$-alkylene), $C_4$-$C_{24}$-alkane-diyl, which is interrupted by one or more oxygen atoms, $C_4$-$C_{20}$-alkane-diyl, which is interrupted by one or more —NH—, —N($C_1$-$C_8$-alkyl)- or —N(hydroxy-$C_1$-$C_8$-alkyl)-, piperazine-N,N'-bis-($C_1$-$C_4$-alkylene) or $C_2$-$C_{10}$-alkane-diyl, which is interrupted by one sulfur atom;
n is 1 or 2;
$R_1$ to $R_4$ and $R_6$ to $R_9$ are each independently from each other H, $C_1$-$C_{12}$-alkyl, $C_3$-$C_{10}$-cycloalkyl, $C_3$-$C_{22}$-alkenyl, $C_1$-$C_{12}$-alkoxy, $C_1$-$C_{12}$-alkylsulfanyl, hydroxy-$C_1$-$C_8$-alkyl, halogen, $NR''_1R''_2$, $NO_2$, CN, phenyl; and
$R'_1$, $R'_2$, $R''_1$ and $R''_2$ are each independently from each other H, $C_1$-$C_{12}$-alkyl, $C_3$-$C_{10}$-cycloalkyl, hydroxy-$C_1$-$C_8$- alkyl, $C_3$-$C_{22}$-alkenyl, $C_6$-$C_{10}$-aryl, which is unsubstituted or substituted by $C_1$-$C_8$-alkyl, $C_1$-$C_8$-alkoxy, halogen or one phenyl, $C_7$-$C_{12}$-aralkyl, carboxy-$C_1$-$C_{12}$-alkyl, $C_1$-$C_{12}$-alkoxycarbonyl-$C_1$-$C_{12}$-alkyl, or carboxy-$C_6$-$C_{10}$-aryl.

Preferred is a composition, which comprises an organic material susceptible to oxidative, thermal or light-induced degradation and a compound of formula I, wherein at formula I
when n is 1,
$R_5$ is H, $C_1$-$C_{30}$-alkyl, $C_3$-$C_{10}$-cycloalkyl, $C_6$-$C_{10}$-aryl, which is unsubstituted or substituted by $C_1$-$C_8$-alkyl, $C_1$-$C_8$-alkoxy, halogen or one phenyl, $C_7$-$C_{13}$-aralkyl, $C_2$-$C_{22}$-alkenyl, $C_3$-$C_{12}$-alkinyl, OH, $C_1$-$C_{30}$-alkyloxy, $C_3$-$C_{10}$-cycloalkyloxy, $C_6$-$C_{12}$-aryloxy, $C_7$-$C_{13}$-aralkyloxy, hydroxy-$C_1$-$C_8$-alkyl, carboxy-$C_1$-$C_{12}$-alkyl, $C_1$-$C_{12}$-alkoxycarbonyl-$C_1$-$C_{12}$-alkyl, $C_2$-$C_{30}$-alkyl, which is interrupted by one or more oxygen atoms, $C_2$-$C_{16}$-alkyl, which is interrupted by one sulfur atom, or $NR'_1R'_2$;
when n is 2,
$R_5$ is $C_1$-$C_{12}$-alkane-diyl, $C_4$-$C_{24}$-alkane-diyl, which is interrupted by one or more oxygen atoms, $C_4$-$C_{20}$-alkane-diyl, which is interrupted by one or more —NH—, —N($C_1$-$C_8$-alkyl)- or —N(hydroxy-$C_1$-$C_8$-alkyl)-, piperazine-N,N'-bis-($C_1$-$C_4$-alkylene) or $C_4$-$C_{10}$-alkane-diyl, which is interrupted by one sulfur atom;
n is 1 or 2;
2 substituents out of $R_1$ to $R_4$ and 2 substituents out of $R_6$ to $R_9$ are H and the other remaining 4 substituents out of $R_1$ to $R_4$ and $R_6$ to $R_9$ are each independently from each other H, $C_1$-$C_{12}$-alkyl, $C_3$-$C_{10}$-cycloalkyl, $C_3$-$C_{22}$-alkenyl, $C_1$-$C_{12}$-alkoxy, $C_1$-$C_{12}$-alkylsulfanyl, hydroxy-$C_1$-$C_8$-alkyl, halogen, $NR''_1R''_2$, $NO_2$, CN, phenyl, phenyloxy; and $R'_1$, $R'_2$, $R''_1$ and $R''_2$ are each independently from each other H, $C_1$-$C_{12}$-alkyl, $C_3$-$C_{10}$-cycloalkyl, hydroxy-$C_1$-$C_8$-alkyl, $C_3$-$C_{22}$-alkenyl, $C_6$-$C_{10}$-aryl, which is unsubstituted or substituted by $C_1$-$C_8$-alkyl, $C_1$-$C_8$-alkoxy, halogen or one phenyl, $C_7$-$C_{12}$-aralkyl, carboxy-$C_1$-$C_{12}$-alkyl, $C_1$-$C_{12}$-alkoxycarbonyl-$C_1$-$C_{12}$-alkyl, or carboxy-$C_6$-$C_{10}$-aryl, or $R'_1$ and $R'_2$ or $R''_1$ and $R''_2$ form together with the nitrogen atom, to which they are attached, a pyrrolidine, a piperidine or a morpholine ring.

Preferred is a composition, which comprises an organic material susceptible to oxidative, thermal or light-induced degradation and a compound of formula I, wherein at formula I
n is 1,
$R_5$ is H, $C_1$-$C_{30}$-alkyl, $C_3$-$C_{10}$-cycloalkyl, $C_6$-$C_{10}$-aryl, which is unsubstituted or substituted by $C_1$-$C_8$-alkyl or $C_1$-$C_8$-alkoxy, $C_7$-$C_{13}$-aralkyl, $C_2$-$C_{22}$-alkenyl, OH, $C_1$-$C_{30}$-alkyloxy, $C_3$-$C_{10}$-cycloalkyloxy, $C_6$-$C_{12}$-aryloxy, $C_7$-$C_{13}$-aralkyloxy, hydroxy-$C_1$-$C_8$-alkyl, carboxy-$C_1$-$C_{12}$-alkyl, $C_1$-$C_{12}$-alkoxycarbonyl-$C_1$-$C_{12}$-alkyl, $C_2$-$C_{30}$-alkyl, which is interrupted by one or more oxygen atoms, or $NR'_1R'_2$;
3 substituents out of $R_1$ to $R_4$ and 2 substituents out of $R_6$ to $R_9$ are H and the other remaining 3 substituents out of $R_1$ to $R_4$ and $R_6$ to $R_9$ are each independently from each other H, $C_1$-$C_{12}$-alkyl, $C_1$-$C_{12}$-alkoxy or halogen; and
$R'_1$ and $R'_2$ are each independently from each other H, $C_1$-$C_{12}$-alkyl, $C_3$-$C_{10}$-cycloalkyl, $C_3$-$C_{22}$-alkenyl, $C_6$-$C_{10}$-aryl, which is unsubstituted or substituted by $C_1$-$C_8$-alkyl or $C_1$-$C_8$-alkoxy, $C_7$-$C_{12}$-aralkyl, or $R'_1$ and $R'_2$ form together with the nitrogen atom, to which they are attached, a pyrrolidine, a piperidine or a morpholine ring.

Preferred is a composition, which comprises an organic material susceptible to oxidative, thermal or light-induced degradation and a compound of formula I, wherein at formula I
when n is 1,
$R_5$ is H, $C_1$-$C_{30}$-alkyl, $C_3$-$C_{10}$-cycloalkyl, $C_6$-$C_{10}$-aryl, which is unsubstituted or substituted by $C_1$-$C_8$-alkyl or $C_1$-$C_8$-alkoxy;
when n is 2,
$R_5$ is $C_1$-$C_{12}$-alkane-diyl or $C_4$-$C_{24}$-alkane-diyl, which is interrupted by one or more oxygen atoms;
n is 1 or 2; and
3 substituents out of $R_1$ to $R_4$ and 2 substituents out of $R_6$ to $R_9$ are H and the other remaining 3 substituents out of $R_1$ to $R_4$ and $R_6$ to $R_9$ are each independently from each other H, $C_1$-$C_{12}$-alkyl, $C_1$-$C_{12}$-alkoxy or halogen.

Preferred is a composition, which comprises an organic material susceptible to oxidative, thermal or light-induced degradation and a compound of formula I, wherein at formula I
n is 1,
$R_5$ is H, $C_1$-$C_{30}$-alkyl, $C_3$-$C_{10}$-cycloalkyl, $C_6$-$C_{10}$-aryl, which is unsubstituted or substituted by $C_1$-$C_8$-alkyl or $C_1$-$C_8$-alkoxy; and
3 substituents out of $R_1$ to $R_4$ and 2 substituents out of $R_6$ to $R_9$ are H and the other remaining 3 substituents out of $R_1$ to $R_4$ and $R_6$ to $R_9$ are each independently from each other H, $C_1$-$C_{12}$-alkyl, $C_1$-$C_{12}$-alkoxy or halogen.

Preferred is a composition, which comprises an organic material susceptible to oxidative, thermal or light-induced degradation and a compound of formula I, wherein at formula I
n is 1,
$R_5$ is H; and
3 substituents out of $R_1$ to $R_4$ and 2 substituents out of $R_6$ to $R_9$ are H and the other remaining 3 substituents out of $R_1$ to $R_4$ and $R_6$ to $R_9$ are each independently from each other H, $C_1$-$C_{12}$-alkyl, $C_1$-$C_{12}$-alkoxy or halogen.

For compositions and preferences thereof as described in this description, very preferred compounds of formula I are compounds (101), (102), (103), (104), (105), (106), (107), (108), (109), (110), (111), (113) and (114). The structures of these compounds are depicted in the respective examples 1 to 11 and 13 to 14.

For compositions and preferences thereof as described in this description, a very preferred compound of formula I is compound (101), for which at formula I n is 1 and $R_1$ to $R_9$ is H. Compound (101) is depicted below.

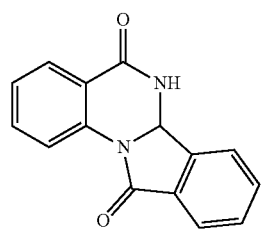

(101)

The employed amount of component b) in regard to component a) varies with the particular organic material susceptible to oxidative, thermal or light-induced degradation and the desired degree of protection.

Preferred is a composition, which comprises an organic material susceptible to oxidative, thermal or light-induced degradation as component a) and a compound of formula I as component b), wherein component b) is contained in an amount of 0.0005% to 10%, in particular from 0.001 to 2%, especially from 0.005 to 1%, based on the weight of component a).

Optionally, a composition comprising an organic material as component a) and a compound of formula I as component b) contains a further additive as component c).

A further additive can be selected from the following list:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example 2,6-di-nonyl-4-methylphenol, 2,4-dimethyl-6-(1'-methyl-undec-1'-yl)phenol, 2,4-dimethyl-6-(1'-methylheptadec-1'-yl)phenol, 2,4-dimethyl-6-(1'-methyltridec-1'-yl)phenol, 2,4-dimethyl-6-(1'-methyl-1'-tetradecyl-methyl)-phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis (3,5-di-tert-butyl-4-hydroxyphenyl) adipate.

1.4. Tocopherols, for example α-tocopherol, β-tocopherol, γ-tocopherol, δ-tocopherol and mixtures thereof (vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl)disulfide.

1.6. Alkylidenebisphenols, for example 2,2'-methylenebis (6-tert-butyl-4-methylphenol), 2,2'-methylenebis(6-tert-butyl-4-ethylphenol), 2,2'-methylenebis[4-methyl-6-(α-methyl-cyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis [6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)-butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis(3,5-di-tert-butyl-4-hydroxyphenyl)-propane, 2,2-bis-(5-tert-butyl-4-hydroxy-2-methylphenyl)-4-n-dodecylmercaptobutane, 1,1,5,5-tetra (5-tert-butyl-4-hydroxy-2-methylphenyl)pentane.

1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzyl-mercaptoacetate.

1.8. Hydroxybenzylated malonates, for example dioctadecyl-2,2-bis(3,5-di-tert-butyl-2-hydroxybenzyl)malonate, di-octadecyl-2-(3-tert-butyl-4-hydroxy-5-methylbenzyl)malonate, di-dodecylmercaptoethyl-2,2-bis(3,5-di-tert-butyl-4-hydroxybenzyl)malonate, bis[4-(1,1,3,3-tetramethylbutyl) phenyl]-2,2-bis(3,5-di-tert-butyl-4-hydroxybenzyl) malonate.

1.9. Aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl-3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl)propionic acid with mono- or polyhydric alcohols, for example with methanol, ethanol, n-octanol, i-octanol, octadecanol, a mixture of linear and branched $C_{13}$-$C_{15}$-alkanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxylethyl)isocyanurate, N,N'-bis-(hydroxylethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane.

1.14. Esters of β-(5-tert-butyl-4-hydroxy-3-methylphenyl) propionic acid with mono- or polyhydric alcohols, for example with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris-(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane; 3,9-bis[2-{3-(3-tert-butyl-4-hydroxy-5-methyl-phenyl)propionyloxy}-1,1-dimethylethyl]-2,4,8,10-tetraoxaspiro[5.5]undecane.

1.15. Esters of β-(3,5-dicyclohexyl-4-hydroxyphenyl)propionic acid with mono- or polyhydric alcohols, for example with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]-octane.

1.16. Esters of 3,5-di-tert-butyl-4-hydroxyphenyl acetic acid with mono- or polyhydric alcohols, for example with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid, for example N,N'-bis(3,5-di-tert-butyl-4-hydroxyphenylpropionyl)hexamethylenediamide, N,N'-bis(3,5-di-tert-butyl-4-hydroxyphenylpropionyl) trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]-propionyloxy)ethyl]oxamide (Naugard XL-1®, supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]-ethane, 1,2-bis(phenylamino)propane, (o-tolyl)biguanide, bis[4-(1,3'-dimethylbutyl)-phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylatedisopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octylphenothiazines, N-allylphenothiazine, N,N,N',N'-tetraphenyl-1,4-diaminobut-2-ene, N,N-bis(2,2,6,6-tetramethylpiperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-ol.

2. UV Absorbers and Light Stabilisers 2.1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxy-phenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis(α,α-dimethylbenzyl)-2'-hydroxy-phenyl)benzotriazole, 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxyl)carbonylethyl]-2'-hydroxy-phenyl)-5-chlorobenzotriazole, 2-(3'-tert-butyl-2'-hydroxy-5'-(2-methoxycarbonylethyl)-phenyl)-5-chlorobenzotriazole, 2-(3'-tert-butyl-2'-hydroxy-5'-(2-methoxycarbonylethyl)-phenyl)benzotriazole, 2-(3'-tert-butyl-2'-hydroxy-5'-(2-octyloxycarbonylethyl)phenyl)-benzotriazole, 2-(3'-tert-butyl-5'-[2-(2-ethylhexyloxyl)carbonylethyl]-2'-hydroxyphenyl)-benzotriazole, 2-(3'-dodecyl-2'-hydroxy-5'-methylphenyl) benzotriazole, 2-(3'-tert-butyl-2'-hydroxy-5'-(2-isooctyloxycarbonylethyl)phenylbenzotriazole, 2,2'-methylenebis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300;

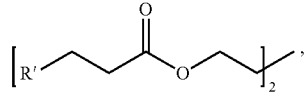

where R'=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)phenyl]benzotriazole; 2-[2'-hydroxy-3'-(1,1,3,3-tetramethylbutyl)-5'-(α,α-dimethylbenzyl)phenyl] benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example 4-tert-butylphenyl salicylate, phenyl salicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate, N-(β-carbomethoxy-β-cyanovinyl)-2-methylindoline and neopentyl tetra(α-cyano-β,β-diphenylacrylate).

2.5. Nickel compounds, for example nickel complexes of 2,2'-thiobis[4-(1,1,3,3-tetra-methylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenylundecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)-sebacate, bis(2,2,6,6-tetramethyl-4-piperidyl)succinate, bis(1,2,2,6,6-pentamethyl-4-piperidyl)sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidypexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butanetetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperid-4-yl) sebacate, bis(1-octyloxy-2,2,6,6-tetramethylpiperid-4-yl) succinate, bis-[2,2,6,6-tetramethyl-1-(undecyloxy)-piperidin-4-yl]carbonate, linear or cyclic condensates of N,N'-bis(2,2,6,6-tetramethyl-4-piperidyl)-hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl) pyrrolidine-2,5-dione, a mixture of 4-hexadecyloxy- and 4-stearyloxy-2,2,6,6-tetramethylpiperidine, a condensate of N,N'-bis(2,2,6,6-tetramethyl-4-piperidypexamethylenediamine and 4-cyclohexylamino-2,6-dichloro-1,3,5-triazine, a condensate of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); a condensate of 1,6-hexanediamine and 2,4,6-trichloro-1,3,5-triazine as well as N,N-dibutylamine and 4-butylamino-2,2,6,6-tetramethylpiperidine (CAS Reg. No. [192268 64-7]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxospiro[4,5]decane, a reaction product of 7,7,9,9-tetramethyl-2-cycloundecyl-1-oxa-3,8-diaza-4-oxospiro-[4,5]decane and epichlorohydrin, 1,1-bis(1,2,2,6,6-pentamethyl-4-piperidyloxycarbonyl)-2-(4-methoxyphenyl)-ethene, N,N'-bisformyl-N,N'-bis(2,2,6,6-tetramethyl-4-piperidyl)hexamethylenediamine, a diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, a reaction product of maleic acid anhydride-α-olefin copolymer with 2,2,6,6-tetramethyl-4-aminopiperidine or 1,2,2,6,6-pentamethyl-4-aminopiperidine, a mixture of oligomeric compounds which are the formal condensation products of N,N'-bis-(2,2,6,6-tetramethyl-1-propoxy-piperidin-4-yl)-hexane-1,6-diamine and 2,4-dichloro-6-{n-butyl-(2,2,6,6-tetramethyl-1-propoxy-piperidin-4-yl)-amino}-[1,3,5] triazine end-capped with 2-chloro-4,6-bis-(di-n-butylamino)-[1,3,5]triazine, a mixture of oligomeric compounds which are the formal condensation products of N,N'-bis-(2,2,6,6-tetramethyl-piperidin-4-yl)-hexane-1,6-diamine and 2,4-dichloro-6-{n-butyl-(2,2,6,6-tetramethyl-piperidin-4-yl)-amino}-[1,3,5]triazine end-capped with 2-chloro-4,6-bis-(di-n-butylamino)-[1,3,5]triazine, 2,4-bis [N-(1-cyclohexyloxy-2,2,6,6-tetramethylpiperidine-4-yl)-N-butylamino]-6-(2-hydroxyethyl)amino-1,3,5-triazine, 1-(2-hydroxy-2-methylpropoxy)-4-octadecanoyloxy-2,2,6,6-tetramethylpiperidine, 5-(2-ethylhexanoyl)oxymethyl-3,3,5-trimethyl-2-morpholinone, Sanduvor (Clariant; CAS Reg. No. 106917-31-1], 5-(2-ethylhexanoyl)-oxymethyl-3,3,5-trimethyl-2-morpholinone, the reaction product of 2,4-bis-[(1-cyclo-hexyloxy-2,2,6,6-piperidine-4-yl)butylamino]-6-chloro-s-triazine with N,N'-bis-(3-amino-propyl) ethylenediamine), 1,3,5-tris(N-cyclohexyl-N-(2,2,6,6-tetramethyl-piperazine-3-one-4-yl)amino)-s-triazine, 1,3,5-tris(N-cyclohexyl-N-(1,2,2,6,6-pentamethylpiperazine-3-one-4-yl)-amino)-s-triazine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propy¬ oxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy)phenyl]-4,6-bis(2,4-dimethyl)-1,3,5-triazine, 2-[2-hydroxy-4-(2-hydroxy-3-octyloxypropyloxy)phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]-phenyl}-4,6-bis¬ (2,4-dimethylphenyl)-1,3,5-triazine.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenyl-propionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)-thiopropionyl dihydrazide.

4. Phosphites and phosphonites, for example triphenyl phosphite, diphenylalkyl phosphites, phenyldialkyl phosphites, tris(nonylphenyl)phosphite, trilauryl phosphite, trioctadecyl phosphite, distearylpentaerythritol diphosphite, tris(2,4-di-tert-butylphenyl)phosphite, diisodecyl pentaerythritol diphosphite, bis(2,4-di-tert-butylphenyl)pentaerythritol diphosphite, bis(2,4-di-cumylphenyl)pentaerythritol diphosphite, bis(2,6-di-tert-butyl-4-methylphenyl)pentaerythritol diphosphite, diisodecyloxypentaerythritol diphosphite, bis (2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tertbutylphenyl) 4,4'-biphenylene diphosphonite, 6-isooctyloxy-2,4,8,10-tetra-tert-butyl-12H-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 6-fluoro-2,4,8,10-tetra-tert-butyl-12-methyl-dibenz[d,g]-1,3,2-dioxaphosphocin, 2,2',2"-nitrilo-[triethyltris(3,3',5,5'-tetra-tert-butyl-1,1'-biphenyl-2,2'-diyl) phosphite], 2-ethylhexyl-(3,3',5,5'-tetra-tert-butyl-1,1'-biphenyl-2,2'-diyl)phosphite, 5-butyl-5-ethyl-2-(2,4,6-tri-tert-butylphenoxy)-1,3,2-dioxaphosphirane.

The following phosphites are especially preferred:

Tris(2,4-di-tert-butylphenyl)phosphite (Irgafos 168, RTM BASF), tris(nonylphenyl)phosphite,

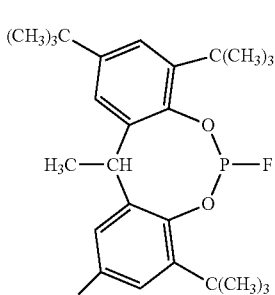
(A)

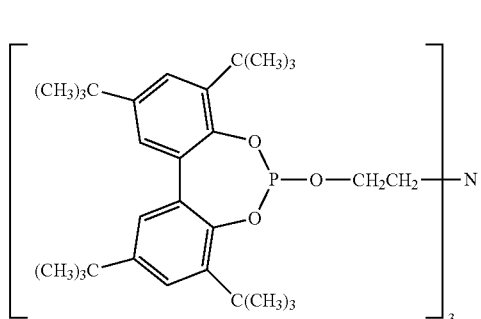
(B)

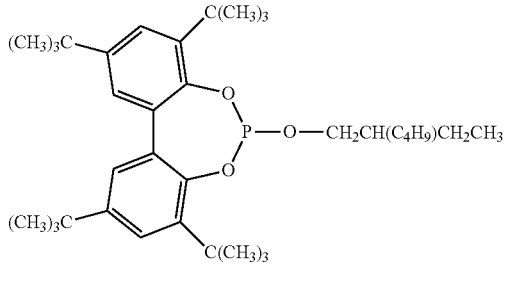
(C)

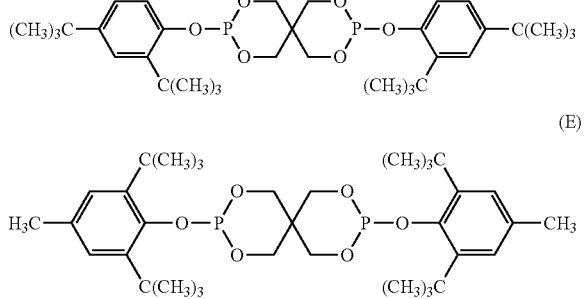
(D)

(E)

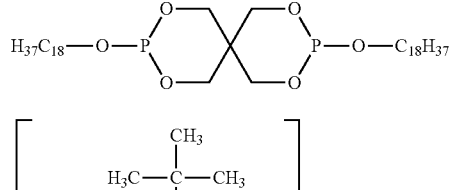
(F)

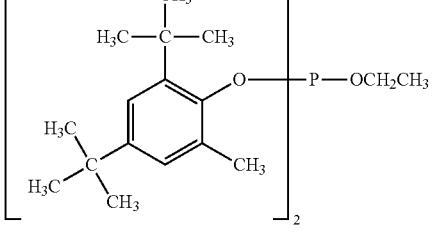
(G)

5. Hydroxylamines and amine N-oxides, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine or N,N-bis-(hydrogenated rape-oil alkyl)-N-methyl-amine N-oxide.

6. Nitrones, for example N-benzyl-alpha-phenylnitrone, N-ethyl-alpha-methylnitrone, N-octyl-alpha-heptylnitrone, N-lauryl-alpha-undecylnitrone, N-tetradecyl-alpha-tridecylnitrone, N-hexadecyl-alpha-pentadecylnitrone, N-octadecyl-alpha-heptadecylnitrone, N-hexadecyl-alpha-heptadecylnitrone, N-ocatadecyl-alpha-pentadecylnitrone, N-heptadecyl-alpha-heptadecylnitrone, N-octadecyl-alpha-hexadecylnitrone, nitrone derived from N,N-dialkylhydroxylamine derived from hydrogenated tallow amine.

7. Thiosynergists, for example dilauryl thiodipropionate, dimistryl thiodipropionate, distearyl thiodipropionate and pentaerythritol tetrakis-[3-(n-lauryl)-propionic acid ester].

8. Peroxide scavengers, for example esters of α-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilizers, for example copper salts in combination with iodides and/or phosphorus compounds and salts of divalent manganese.

10. Acid scavengers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate and potassium palmitate, antimony pyrocatecholate and zinc pyrocatecholate.

11. Benzofuranones and indolinones, for example those disclosed in U.S. Pat. Nos. 4,325,863; 4,338,244; 5,175,312; 5,216,052; 5,252,643; DE-A-4316611; DE-A-4316622; DE-A-4316876; EP-A-0589839 or EP-A-0591102 or 3-[4-(2-acetoxy-ethoxy)phenyl]-5,7-di-tert-butylbenzofuran-2-one, 5,7-di-tert-butyl-3-[4-(2-stearoyloxy-ethoxy)phenyl]benzofuran-2-one, 3,3'-bis[5,7-di-tert-butyl-3-(4-[2-hydroxyethoxy]-phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butylbenzofuran-2-one, 3-(3,5- dimethyl-4-pivaloyloxyphenyl)-5,7-di-tert-butylbenzofuran-2-one, 3-(3,4-dimethylphenyl)-5,7-di-tert-butylbenzofuran-2-one, 3-(2,3-dimethylphenyl)-5,7-di-tert-butylbenzofuran-2-one and 3-(2-acetoxy-4-(1,1,3,3-tetramethyl-butyl)-phenyl)-5-(1,1,3,3-tetramethyl-butyl)-benzofuran-2-one.

12. Nucleating agents, for example inorganic substances, such as talcum, metal oxides, such as titanium dioxide or magnesium oxide, phosphates, carbonates or sulfates of, preferably, alkaline earth metals; organic compounds, such as mono- or polycarboxylic acids and the salts thereof, e.g. 4-tert-butylbenzoic acid, adipic acid, diphenylacetic acid, sodium succinate or sodium benzoate; polymeric compounds, such as ionic copolymers (ionomers), Irgaclear XT 386 (RTM BASF), 1,3:2,4-bis(3',4'-dimethylbenzylidene)-sorbitol, 1,3:2,4-di(paramethyldibenzylidene)-sorbitol, and 1,3:2,4-di(benzylidene)sorbitol.

13. Fillers and reinforcing agents, for example calcium carbonate, silicates, glass fibres, glass beads, asbestos, talc, kaolin, bentonite, mica, hydrotalcite, barium sulfate, metal oxides and hydroxides, carbon black, graphite, wood flour and flours or fibers of other natural products, synthetic fibers.

14. Other additives, for example plasticisers, lubricants, rheology additives, catalysts, flow-control agents, optical brighteners, flameproofing agents, antistatic agents and blowing agents.

It has also been surprisingly found that many compounds of formula I in combination with a further additive are very effective for stabilization of an organic material against degradation by heat, light and/or oxidation, in particular in combination with a phenolic antioxidant or a phosphite or phosphonite as a further additive. It often turns out that the presence of compounds of formula I allows to reduce the amount of the further additive in excess of a mere 1 to 1 substitution based on weight of the further additive.

Preferred is a composition, which comprises an organic material susceptible to oxidative, thermal or light-induced degradation as component a), a compound of formula I as component b) and a further additive as component c).

Preferred is a composition, wherein the weight ratio of component b) to component c) is from 10:1 to 1:30, in particular from 4:1 to 1:20, especially from 2:1 to 1:10, and wherein the overall amount of component b) and component c) is below 80%, especially 50%, by weight of component a).

Preferred is a composition, wherein the weight ratio of component b) to component c) is from 4:1 to 1:20 and the combined amount of component b) and component c) is below 80% based on the weight of component a).

Preferred is a composition, which comprises as component c) a further additive, which is an antioxidant, an UV absorber, a hindered amine light stabilizer, a nickel compound, a metal deactivator, a phosphite or phosphonite, a hydroxylamine or amine N-oxide, a thiosynergist, a peroxide scavenger, a nucleating agent, a filler or reinforcing agent.

Preferred is a composition, which comprises as component c) a further additive, which is a phosphite or phosphonite, an acid scavenger, a phenolic antioxidant or an aminic antioxidant.

Preferred is a composition, which comprises
a) an organic material susceptible to oxidative, thermal or light-induced degradation,
b) a compound of formula I, and
c) a further additive, which is a phenolic antioxidant or a phosphite or phosphonite.

Preferred is a composition, which comprises as component c) a phenolic antioxidant.

Preferred is a composition, which comprises as component c) a phenolic antioxidant, which is an ester of β-(3,5-di-tert-butyl-4-hydroxyphenyl)propionic acid.

A phenolic antioxidant of special relevance is a compound as depicted

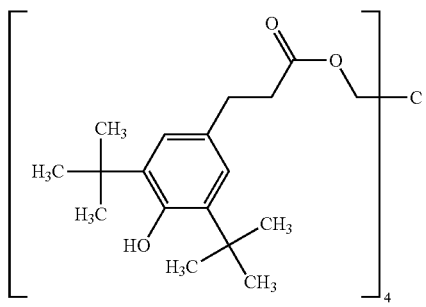

and for which one chemical name is tetrakis-[β-(3,5-di-tert-butyl-4-hydroxyphenyl)-propionyloxymethyl]methane or alternatively tetrakis-[3-(3,5-di-tert-butyl-4-hydroxy-phenyl)-propionyloxymethyl]methane. It is contained in the commercial product Irganox 1010 (RTM BASF).

Another phenolic antioxidant of special relevance is a compound as depicted

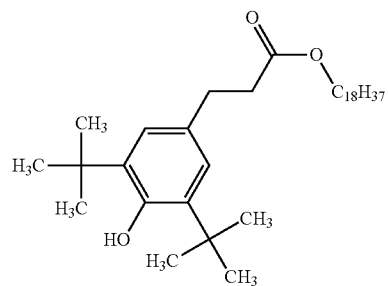

and for which one chemical name is stearyl β-(3,5-di-tert-butyl-4-hydroxyphenyl)-propionate or alternatively stearyl 3-(3,5-di-tert-butyl-4-hydroxyphenyl)-propionate. It is contained in the commercial product Irganox 1076 (RTM BASF).

Preferred is a composition, which comprises as component c) a phenolic antioxidant, which is tetrakis-[β-(3,5-di-tert-butyl-4-hydroxyphenyl)-propionyloxymethyl]methane or stearyl β-(3,5-di-tert-butyl-4-hydroxyphenyl)-propionate.

Preferred is a composition, which comprises as component c) a phosphite or phosponite.

A phosphite of special relevance is a compound as depicted

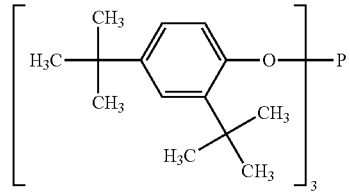

and for which one chemical name is tris-(2,4-di-tert-butyl-4-hydroxyphenyl)phosphite. It is contained in the commercial product Irgafos 168 (RTM BASF).

Preferred is a composition, which comprises as component c) a phosphite, which is tris-(2,4-di-tert-butyl-4-hydroxyphenyl)phosphite.

Optionally, a composition comprising an organic material susceptible to oxidative, thermal or light-induced degradation as component a), a compound of formula I as component b) and a further additive as component c) contains a second further additive as component d).

Preferred is a composition, which comprises an organic material susceptible to oxidative, thermal or light-induced degradation as component a), a compound of formula I as component b), a further additive as component c) and a second further additive as component d).

Preferred is a composition, wherein the weight ratio of component b) to component d) is from 10:1 to 1:30, in particular from 4:1 to 1:20, especially from 2:1 to 1:10, and wherein the overall amount of component b), component c) and component d) is below 50% by weight of component a).

Preferred is a composition, which comprises a component a), a component b), as component c) a further additive, which is selected from the group consisting of a phosphite or phosphonite, an acid scavenger, a phenolic antioxidant and an aminic antioxidant, and as component d) a second further additive.

Preferred is a composition, which comprises as component d) a second further additive, which is a phosphite or phosphonite, an acid scavenger, a phenolic antioxidant or an aminic antioxidant; with the proviso that component d) is a different substance than component c).

Preferred is a composition, which comprises a component a), a component b), a component c) and a component d), wherein component c) and component d) are independently from each other a phosphite or phosphonite, an acid scavenger, a phenolic antioxidant or an aminic antioxidant.

Preferred is a composition, which comprises a component a), a component b), a component c) and a component d), wherein component c) and component d) are independently from each other a phosphite or phosphonite, an acid scavenger, a phenolic antioxidant or an aminic antioxidant; with the proviso that component d) is a different substance than component c).

Preferred is a composition, which comprises a component a), a component b), as component c) a phenolic antioxidant and as component d) an aminic antioxidant.

Preferred is a composition, which comprises a component a), a component b), as component c) a phenolic antioxidant and as component d) a phosphite or phosphonite.

Preferred is a composition, which comprises
a) an organic material susceptible to oxidative, thermal or light-induced degradation,
b) a compound of formula I,
c) a further additive, which is a phenolic antioxidant, and
d) a second further additive, which is a phosphite or phosphonite.

Preferred is a composition, which comprises
a) an organic material susceptible to oxidative, thermal or light-induced degradation,
b) a compound of formula I,
c) a further additive, which is a phenolic antioxidant, which is tetrakis-[β-(3,5-di-tert-butyl-4-hydroxyphenyl)-propionyloxymethyl]methane or stearyl β-(3,5-di-tert-butyl-4-hydroxyphenyl)-propionate, and
d) a second further additive, which is a phosphite or phosphonite.

Preferred is a composition, which comprises
a) an organic material susceptible to oxidative, thermal or light-induced degradation,
b) a compound of formula I,
c) a further additive, which is a phenolic antioxidant, and
d) a second further additive, which is a phosphite, which is tris-(2,4-di-tert-butyl)phosphite.

Preferred is a composition, which comprises
a) an organic material susceptible to oxidative, thermal or light-induced degradation,
b) a compound of formula I,
c) a further additive, which is a phenolic antioxidant, which is tetrakis-[β-(3,5-di-tert-butyl-4-hydroxyphenyl)-propionyloxymethyl]methane or stearyl β-(3,5-di-tert-butyl-4-hydroxyphenyl)-propionate, and
d) a second further additive, which is a phosphite, which is tris-(2,4-di-tert-butyl)phosphite.

The above described preferences for an organic material susceptible to oxidative, thermal or light-induced degradation as component a) and of a compound of formula I as component b) apply also to the further embodiments of the invention. This applies also in regard to the optional presence of a further additive as component c) and the optional presence of a second further additive as component d).

A further embodiment of the invention relates to a process for protection of an organic material susceptible to oxidative, thermal or light-induced degradation, i.e. component a), which comprises the step of incorporation into or application onto an organic material, a compound of formula I, i.e. component b).

The incorporation or application of component b) can be carried out in a processing apparatus, in particular a heatable container equipped with a stirrer, which can preferably be closed. A heatable container equipped with a stirrer is for example a kneader, extruder, mixer or stirred vessel. Specific examples thereof are a single-screw extruder, contrarotating and corotating twin-screw extruder, planetary-gear extruder, ring extruder or co-kneader. It is also possible to use a processing apparatus, which contains at least one gas removal compartment to which a vacuum can be applied and/or which can be set under an atmosphere, wherein the oxygen content is low or oxygen is absent. Component b) can be added directly into the processing apparatus.

Component b) can be incorporated or applied to at any stage of processing of component a). If component a) is a polymer, the stage is in particular prior to or during a shaping operation of component a) in the processing apparatus.

Component b) can be incorporated or applied in the form of a dry powder, in the form of a melt, in encapsulated form such as encapsulation in a wax or an auxiliary polymer or in the form of a wet mixture such as a solution, dispersion or suspension for example in an inert solvent, water or oil. A dispersing or suspension agent can be present in the case of a wet mixture of component b).

Component b) can also be incorporated or applied by spraying onto component a).

In case that component a) is a polymer, a further possibility for incorporation or application of component b) to component a) is addition before, during or directly after the polymerization of the corresponding starting materials, e.g. monomers, of component a). For example, spraying during the deactivation of the polymerization catalysts is partitularly advantageous. If crosslinking takes place during formation of component a), incorporation or application prior to crosslinking is preferred.

In case that component a) is a polymer, the process of incorporation or application is preferably a moulding process, in particular an injection-moulding, blow-moulding, compression-moulding, roto-moulding, slush-moulding or extrusion-moulding.

Preferred is a process, wherein the organic material susceptible to oxidative, thermal or light-induced degradation is a polymer, and which comprises the step of incorporation of a compound of formula I into the organic material and wherein a part or the complete incorporation takes place at a temperature in the range from 135 to 350° C., preferably from 150° C. to 140° C., in particular from 180° C. to 330° C. and very especially from 190° C. to 320° C.

Preferred is a process, wherein component b) is incorporated or applied to in an extruder during processing of component a), which is a polymer.

In case of a further additive and optionally a second further additive, i.e. component c) or components c) and d), component b) and the further additive or the second further additive can be incorporated into or applied onto component a) individually or mixed with one another. If desired, the individual components can be mixed with one another before incorporation into component a) for example by dry blending, compaction, melting, encapsulation by a wax or polymer or as wet mixture in the form of solutions, dispersions or suspensions for example in an inert solvent, water or oil.

Component b) and a further additive and optionally a second further additive can also be added to component a) in the form of a masterbatch (concentrate), which contains the component b), a further additive, optionally a second further additive and a masterbatch polymer. The component b) and a further additive and optionally a second further additive are incorporated into the masterbatch in a concentration of, for example, from 1% to 40% and preferably 2% to 20% by weight of the masterbatch. The masterbatch polymer content is the difference towards 100% by weight of the masterbatch. The masterbatch polymer must not be necessarily the same polymer as component a) in case the latter one is a polymer.

A further embodiment of the invention relates to an additive composition, which comprises
b) a compound of formula I, and
c) a further additive selected from a group consisting of a phosphite or phosphonite, an acid scavenger, a phenolic antioxidant or an aminic antioxidant.

Preferred is a composition, wherein the weight ratio of component b) to component c) is from 10:1 to 1:30, in particular from 4:1 to 1:20, especially from 2:1 to 1:10.

Preferred is an additive composition, wherein the weight ratio of component b) to component c) is from 10:1 to 1:30, in particular from 4:1 to 1:20, especially from 2:1 to 1:10.

Preferred is an additive composition, which comprises
b) a compound of formula I, and
c) a further additive, which is a phenolic antioxidant or a phosphite or phosphonite.

Preferred is an additive composition, which comprises
b) a compound of formula I, and
c) a further additive, which is a phenolic antioxidant.

Preferred is an additive composition, which comprises
b) a compound of formula I, and
c) a further additive, which is a phosphite or phosphonite.

Preferred is an additive composition, which comprises
b) a compound of formula I, and
c) a further additive, which is tetrakis-[β-(3,5-di-tert-butyl-4-hydroxyphenyl)-propionyloxymethyl]methane, stearyl β-(3,5-di-tert-butyl-4-hydroxyphenyl)-propionate or tris-(2,4-di-tert-butyl)phosphite.

Preferred is an additive composition, which comprises as component d) a second further additive.

Preferred is an additive composition, which comprises
b) a compound of formula I,
c) a further additive selected from a group consisting of a phosphite or phosphonite, an acid scavenger, a phenolic antioxidant or an aminic antioxidant, and
d) a second further additive selected from a group consisting of a phosphite or phosphonite, an acid scavenger, a phenolic antioxidant or an aminic antioxidant.

Preferred is an additive composition, which comprises
b) a compound of formula I,
c) a further additive selected from a group consisting of a phosphite or phosphonite, an acid scavenger, a phenolic antioxidant or an aminic antioxidant, and
d) a second further additive selected from a group consisting of a phosphite or phosphonite, an acid scavenger, a phenolic antioxidant or an aminic antioxidant; with the proviso that component c) is a different substance than component d).

Preferred is a composition, wherein the weight ratio of component b) to component c) is from 10:1 to 1:30, in particular from 4:1 to 1:20, especially from 2:1 to 1:10, and wherein the weight ratio of component b) to component d) is from 10:1 to 1:30, in particular from 4:1 to 1:20, especially from 2:1 to 1:10.

Preferred is an additive composition, wherein the weight ratio of component b) to component c) is from 10:1 to 1:30, in particular from 4:1 to 1:20, especially from 2:1 to 1:10, and wherein the weight ratio of component b) to component d) is from 10:1 to 1:30, in particular from 4:1 to 1:20, especially from 2:1 to 1:10.

Preferred is an additive composition, which comprises
b) a compound of formula I,
c) a further additive, which is a phenolic antioxidant, and
d) a second further additive, which is a phosphite or phosphonite.

Preferred is an additive composition, which comprises
b) a compound of formula I,
c) a further additive, which is tetrakis-[β-(3,5-di-tert-butyl-4-hydroxyphenyl)-propionyloxymethyl]methane or stearyl 0-(3,5-di-tert-butyl-4-hydroxyphenyl)-propionate, and
d) a second further additive, which is a phosphite or phosphonite.

Preferred is an additive composition, which comprises
b) a compound of formula I,
c) a further additive, which is a phenolic antioxidant, and
d) a second further additive, which is tris-(2,4-di-tert-butyl) phosphite.

Preferred is an additive composition, which comprises
b) a compound of formula I,
c) a further additive, which is tetrakis-[β-(3,5-di-tert-butyl-4-hydroxyphenyl)-propionyloxymethyl]methane or stearyl 0-(3,5-di-tert-butyl-4-hydroxyphenyl)-propionate, and
d) a second further additive, which is tris-(2,4-di-tert-butyl) phosphite.

A further embodiment of the invention relates to an article, which is made from a composition comprising
a) an organic material susceptible to oxidative, thermal or light-induced degradation, which is a polymer, with the proviso that the polymer is not a polypeptide, agar-agar or a component of agar-agar, and
b) a compound of formula I.

The composition can be advantageously used for the preparation of various shaped articles. Examples for such an article are:

I-1) Floating devices, marine applications, pontoons, buoys, plastic lumber for decks, piers, boats, kayaks, oars, and beach reinforcements.

I-2) Automotive applications, in particular bumpers, dashboards, battery, rear and front linings, moldings parts under the hood, hat shelf, trunk linings, interior linings, air bag covers, electronic moldings for fittings (lights), panes for dashboards, headlamp glass, instrument panel, exterior linings, upholstery, automotive lights, head lights, parking lights, rear lights, stop lights, interior and exterior trims; door panels; gas tank; glazing front side; rear windows; seat backing, exterior panels, wire insulation, profile extrusion for sealing, cladding, pillar covers, chassis parts, exhaust systems, fuel filter/filler, fuel pumps, fuel tank, body side mouldings, convertible tops, exterior mirrors, exterior trim, fasteners/fixings, front end module, glass, hinges, lock systems, luggage/roof racks, pressed/stamped parts, seals, side impact protection, sound deadener/insulator and sunroof.

I-3) Road traffic devices, in particular sign postings, posts for road marking, car accessories, warning triangles, medical cases, helmets, tires.

I-4) Devices for plane, railway, motor car (car, motorbike, trucks) including furnishings.

I-5) Devices for space applications, in particular rockets and satellites, e.g. reentry shields.

I-6) Devices for architecture and design, mining applications, acoustic quietized systems, street refuges, and shelters.

II-1) Appliances, cases and coverings in general and electric/electronic devices (personal computer, telephone, portable phone, printer, television-sets, audio and video devices), flower pots, satellite TV bowl, and panel devices.

II-2) Jacketing for other materials such as steel or textiles.

II-3) Devices for the electronic industry, in particular insulation for plugs, especially computer plugs, cases for electric and electronic parts, printed boards, and materials for electronic data storage such as chips, check cards or credit cards.

II-4) Electric appliances, in particular washing machines, tumblers, ovens (microwave oven), dish-washers, mixers, and irons.

II-5) Covers for lights (e.g. street-lights, lamp-shades).

II-6) Applications in wire and cable (semi-conductor, insulation and cable-jacketing).

II-7) Foils for condensers, refrigerators, heating devices, air conditioners, encapsulating of electronics, semi-conductors, coffee machines, and vacuum cleaners.

III-1) Technical articles such as cogwheel (gear), slide fittings, spacers, screws, bolts, handles, and knobs.

III-2) Rotor blades, ventilators and windmill vanes, solar devices, swimming pools, swimming pool covers, pool liners, pond liners, closets, wardrobes, dividing walls, slat walls, folding walls, roofs, shutters (e.g. roller shutters), fittings, connections between pipes, sleeves, and conveyor belts.

III-3) Sanitary articles, in particular shower cubicles, lavatory seats, covers, and sinks.

III-4) Hygienic articles, in particular diapers (babies, adult incontinence), feminine hygiene articles, shower curtains, brushes, mats, tubs, mobile toilets, tooth brushes, and bed pans.

III-5) Pipes (cross-linked or not) for water, waste water and chemicals, pipes for wire and cable protection, pipes for gas, oil and sewage, guttering, down pipes, and drainage systems.

III-6) Profiles of any geometry (window panes) and siding.

III-7) Glass substitutes, in particular extruded or co-extruded plates, glazing for buildings (monolithic, twin or multiwall), aircraft, schools, extruded sheets, window film for architectural glazing, train, transportation, sanitary articles, and greenhouse.

III-8) Plates (walls, cutting board), extrusion-coating (photographic paper, tetrapack and pipe coating), silos, wood substitute, plastic lumber, wood composites, walls, surfaces, furniture, decorative foil, floor coverings (interior and exterior applications), flooring, duck boards, and tiles.

III-9) Intake and outlet manifolds.

III-10) Cement-, concrete-, composite-applications and covers, siding and cladding, hand rails, banisters, kitchen work tops, roofing, roofing sheets, tiles, and tarpaulins.

IV-1) Plates (walls and cutting board), trays, artificial grass, astroturf, artificial covering for stadium rings (athletics), artificial floor for stadium rings (athletics), and tapes.

IV-2) Woven fabrics continuous and staple, fibers (carpets/hygienic articles/geotextiles/monofilaments; filters; wipes/curtains (shades)/medical applications), bulk fibers (applications such as gown/protection clothes), nets, ropes, cables, strings, cords, threads, safety seat-belts, clothes, underwear, gloves; boots; rubber boots, intimate apparel, garments, swimwear, sportswear, umbrellas (parasol, sunshade), parachutes, paraglides, sails, "balloon-silk", camping articles, tents, airbeds, sun beds, bulk bags, and bags. Non-woven fabrics such as medical fabrics and related apparel, industrial apparel, outdoor fabrics, in-home furnishing and construction fabrics.

IV-3) Membranes, insulation, covers and seals for roofs, tunnels, dumps, ponds, dumps, walls roofing membranes, geomembranes, swimming pools, curtains (shades)/sunshields, awnings, canopies, wallpaper, food packing and wrapping (flexible and solid), medical packaging (flexible & solid), airbags/safety belts, arm- and head rests, carpets, centre console, dashboard, cockpits, door, overhead console module, door trim, headliners, interior lighting, interior mirrors, parcel shelf, rear luggage cover, seats, steering column, steering wheel, textiles, and trunk trim.

V) Films (packaging, dump, laminating, agriculture and horticulture, greenhouse, mulch, tunnel, silage), bale wrap, swimming pools, waste bags, wallpaper, stretch film, raffia, desalination film, batteries, and connectors.

VI-1) Food packing and wrapping (flexible and solid), bottles.

VI-2) Storage systems such as boxes (crates), luggage, chest, household boxes, pallets, shelves, tracks, screw boxes, packs, and cans.

VI-3) Cartridges, syringes, medical applications, containers for any transportation, waste baskets and waste bins, waste bags, bins, dust bins, bin liners, wheely bins, container in general, tanks for water/used water/chemistry/gas/oil/gasoline/diesel; tank liners, boxes, crates, battery cases, troughs, medical devices such as piston, ophthalmic applications, diagnostic devices, and packing for pharmaceuticals blister.

VII-1) Extrusion coating (photo paper, tetrapack, pipe coating), household articles of any kind (e.g. appliances, thermos bottle/clothes hanger), fastening systems such as plugs, wire and cable clamps, zippers, closures, locks, and snap-closures.

VII-2) Support devices, articles for the leisure time such as sports and fitness devices, gymnastics mats, ski-boots, inline-skates, skis, big foot, athletic surfaces (e.g. tennis grounds); screw tops, tops and stoppers for bottles, and cans.

VII-3) Furniture in general, foamed articles (cushions, impact absorbers), foams, sponges, dish clothes, mats, garden chairs, stadium seats, tables, couches, toys, building kits (boards/figures/balls), playhouses, slides, and play vehicles.

VII-4) Materials for optical and magnetic data storage.

VII-5) Kitchen ware (eating, drinking, cooking, storing).

VII-6) Boxes for CD's, cassettes and video tapes; DVD electronic articles, office supplies of any kind (ball-point pens, stamps and ink-pads, mouse, shelves, tracks), bottles of any volume and content (drinks, detergents, cosmetics including perfumes), and adhesive tapes.

VII-7) Footwear (shoes/shoe-soles), insoles, spats, adhesives, structural adhesives, food boxes (fruit, vegetables, meat, fish), synthetic paper, labels for bottles, couches, artificial joints (human), printing plates (flexographic), printed circuit boards, and display technologies.

VII-8) Devices of filled polymers (talc, chalk, china clay (kaolin), wollastonite, pigments, carbon black, $TiO_2$, mica, nanocomposites, dolomite, silicates, glass, asbestos).

Preferred is an article, which is a film, pipe, profile, bottle, tank, container or fiber.

Preferred is an article, which is moulded. In particular, the moulding is effected by injection, blow, compression, roto-moulding, slush-moulding or extrusion.

A further embodiment to the invention relates to the use of a compound of formula I, i.e. component b), for stabilizing an organic material susceptible to oxidative, thermal or light-induced degradation, which is a polymer, an oligohydroxy compound, a wax, a fat or a mineral oil, with the proviso that the polymer is not a polypeptide, agar-agar or a component of agar-agar and the oligohydroxy compound is not glucose or a component of agar-agar, i.e. component a), against degradation by oxidation, heat or light.

Preferred is the use of component b) for stabilizing a polyurethane in the form of a foam against scorching.

Preferred is the use of a compound of formula I for stabilizing an organic material susceptible to oxidative, thermal or light-induced degradation in combination with a further additive against degradation by oxidation, heat or light.

Preferred is the use of a compound of formula I for stabilizing an organic material susceptible to oxidative, thermal or light-induced degradation in combination with a further additive, which is a phenolic antioxidant or a phosphite or phosphonite, against degradation by oxidation, heat or light.

Preferred is the use of a compound of formula I for stabilizing an organic material susceptible to oxidative, thermal or light-induced degradation in combination with a further additive, which is a phenolic antioxidant, and a second further additive, which is a phosphite or phosphonite, against degradation by oxidation, heat or light.

Preferred is the use of a compound of formula I for stabilizing an organic material susceptible to oxidative, thermal or light-induced degradation, which is a polyolefin or a copolymer thereof, in combination with a further additive, which is a phenolic antioxidant, and a second further additive, which is a phosphite or phosphonite, against degradation by oxidation, heat or light.

Processing of a component a) is characterized as short-term exposure of the component a) to heat, for example to a temperature in the range of 135° C. to 150° C., in particular from 150° C. to 340° C., during the time of processing of component a). The time of processing is short in comparison to for example the possible time of usage. Usage takes typically place at a temperature, for example 0° C. to 50° C., which is below the temperature during processing.

Preferred is the use of component b) for stabilizing a component a) against oxidative or thermal degradation during processing.

Compounds of formula I are partly known and partly new. Several synthetic routes to known compounds of formula I are described in literature.

Compounds of formula I can be prepared by cyclocondensation of an anthranilic acid amide derivative of formula II with a formylbenzoic acid derivative of formula III

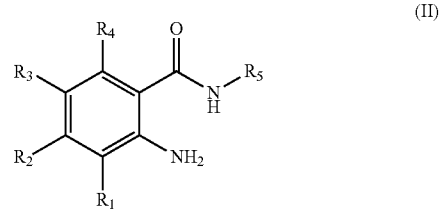

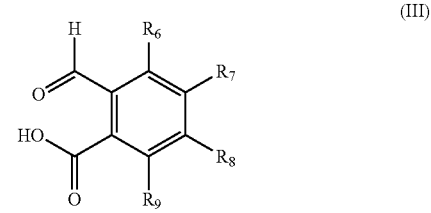

in the prescence of a solvent, wherein the substituents $R_1$ to $R_9$ are defined as in formula I.

Preferred are organic solvents, especially dimethylformamide, dimethylacetamide and ethoxyethanol.

A further embodiment of the invention relates to a compound of formula I

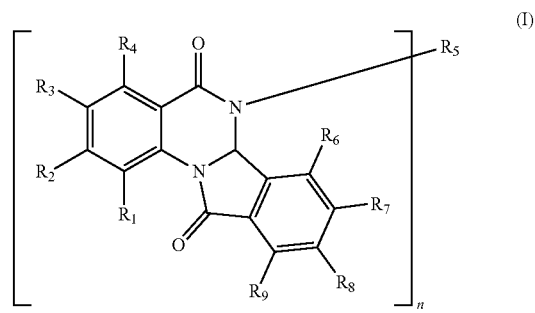

wherein n is 1, $R_5$ is $C_1$-$C_{30}$-alkyloxy, $C_3$-$C_{10}$-cycloalkyloxy, $C_6$-$C_{12}$-aryloxy, $C_7$-$C_{13}$-aralkyloxy or $NR'_1R'_2$;

3 substituents out of $R_1$ to $R_4$ and 2 substituents out of $R_6$ to $R_9$ are H and the other remaining 3 substituents out of $R_1$ to $R_4$ and $R_6$ to $R_9$ are each independently from each other H, $C_1$-$C_{12}$-alkyl, $C_1$-$C_{12}$-alkoxy or halogen; and $R'_1$ and $R'_2$ are each independently from each other H, $C_1$-$C_{12}$-alkyl, $C_3$-$C_{10}$-cycloalkyl, $C_3$-$C_{22}$-alkenyl, $C_6$-$C_{10}$-aryl, $C_7$-$C_{12}$-aralkyl, or $R'_1$ and $R'_2$ form together with the nitrogen atom, to which they are attached, a pyrrolidine, a piperidine or a morpholine ring, with the proviso that $R'_1$ and $R'_2$ are not both $C_1$-alkyl.

The following examples illustrate further the invention without limiting it. Percentage values are percentage by weight if not stated differently.

EXAMPLE 1

Preparation of Compound (101)

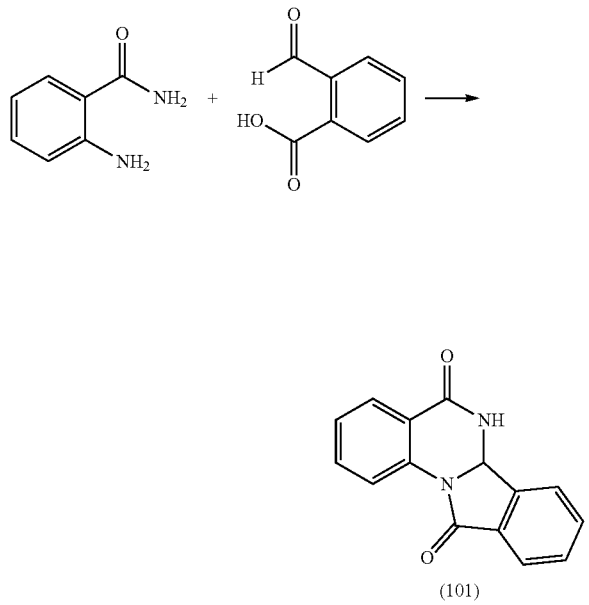

89.8 g (0.65 mol) anthranilic acid amide and 100.0 g (0.65 mol) phthalaldehydic acid are mixed with 900 ml DMA and heated under stirring at 170° C. for 4 h. After cooling to 10° C. 400 ml dichloromethane are added, the white precipitate is filtered on a suction filter and washed twice with 100 ml dichloromethane. The product is dried at 50° C. under vacuum overnight. Yield 138.0 g (85% of theory), white crystals, mp. 286° C.

$^1$H-NMR ([ppm], DMSO-d6): 6.50 (s, 1 H, CH), 7.35-8.05 (m, 8 H, arom. H), 9.45 (s, 1 H, NH)

LC/MS (ACPI pos. mode): [M+1]=251

EXAMPLE 2

Preparation of Compound (102)

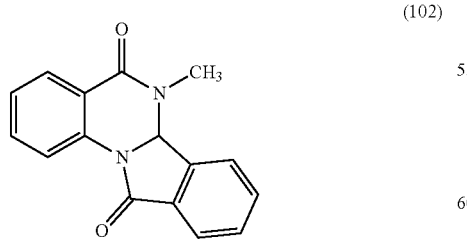

Preparation from 2-amino-N-methyl-benzamide and phthalaldehydic acid in analogy to compound (101)/yield: 93% of theory/mp. 183° C./LC/MS (ACPI pos. mode): [M+1]=265.

EXAMPLE 3

Preparation of Compound (103)

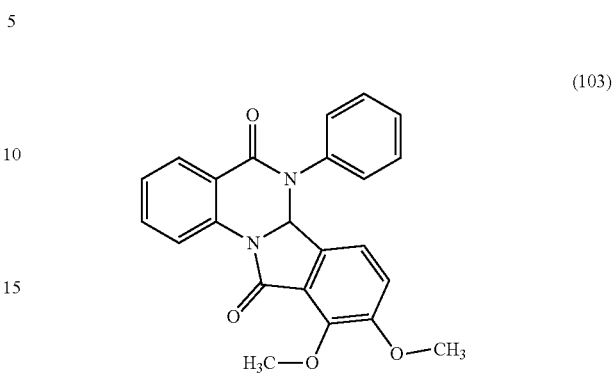

Preparation from 2-amino-N-phenyl-benzamide and 6-formyl-2,3-dimethoxy-benzoic acid in analogy to compound (101)/yield: 100% of theory/mp. 221° C./LC/MS (ACPI pos. mode): [M+1]=387.

EXAMPLE 4

Preparation of Compound (104)

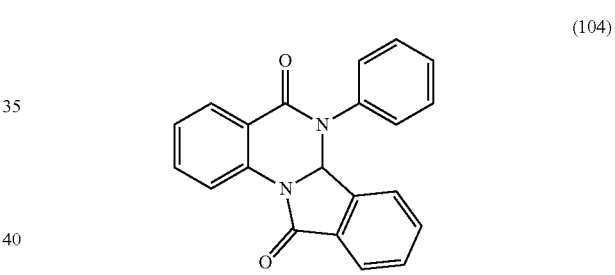

Preparation from 2-amino-N-phenyl-benzamide and phthalaldehydic acid in analogy to compound (101)/yield: 68% of theory/mp. 202° C./LC/MS (ACPI pos. mode): [M+1]=327.

EXAMPLE 5

Preparation of Compound (105)

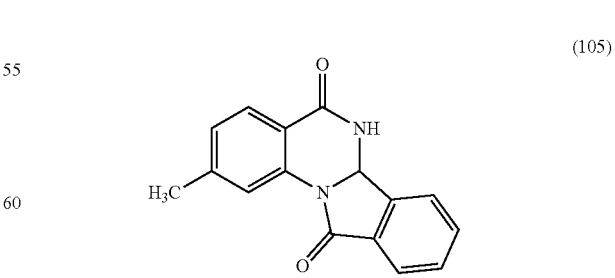

Preparation from 2-amino-4-methyl-benzamide and phthalaldehydic acid in analogy to compound (101)/yield: 85% of theory/mp. 257° C./LC/MS (ACPI pos. mode): [M+1]=265.

EXAMPLE 6

Preparation of Compound (106)

(106)

Preparation from 2-amino-5-chloro-benzamide and phthalaldehydic acid in analogy to compound (101)/yield: 100% of theory/mp. 285° C./LC/MS (ACPI pos. mode): [M+1]=285.

EXAMPLE 7

Preparation of Compound (107)

(107)

Preparation from 2-amino-5-chloro-benzamide and 6-formyl-2,3-dimethoxy-benzoic acid in analogy to compound (101)/yield: 90% of theory/mp. 300° C./LC/MS (ACPI pos. mode): [M+1]=345.

EXAMPLE 8

Preparation of Compound (108)

(108)

Preparation from anthranilic acid amide and 6-formyl-2,3-dimethoxy-benzoic acid in analogy to compound (101)/yield: 100% of theory/mp. 290° C./LC/MS (ACPI pos. mode): [M+1]=311.

EXAMPLE 9

Preparation of Compound (109)

(109)

Preparation from 2-amino-N-dodecyl-benzamide and 6-formyl-2,3-dimethoxy-benzoic acid in analogy to compound (101)/yield: 46% of theory/mp. 93° C./LC/MS (ACPI pos. mode): [M+1]=419.

EXAMPLE 10

Preparation of Compound (110)

(110)

Preparation from 2-amino-4-methyl-benzamide and 6-formyl-2,3-dimethoxy-benzoic acid in analogy to compound (101)/yield: 83% of theory/mp. 293° C./LC/MS (ACPI pos. mode): [M+1]=325.

EXAMPLE 11

Preparation of Compound (111)

(111)

Preparation from 2-amino-N-hexyl-benzamide and phthalaldehydic acid in analogy to compound (101)/yield: 53% of theory/mp. 66° C./LC/MS (ACPI pos. mode): [M+1]=335.

EXAMPLE 12

Preparation of Compound (112)

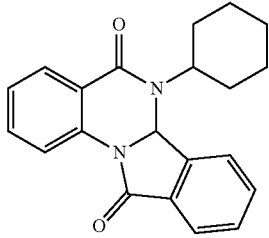
(112)

Preparation from 2-amino-N-cyclohexyl-benzamide and phthalaldehydic acid in analogy to compound (101)/yield: 36% of theory/mp. 175° C./LC/MS (ACPI pos. mode): [M+1]=333.

EXAMPLE 13

Preparation of Compound (113)

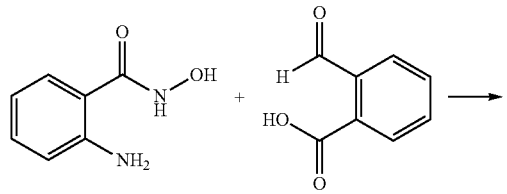

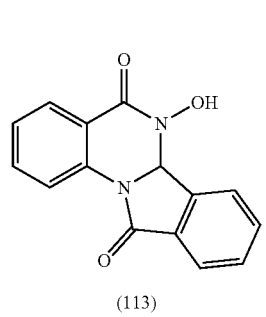
(113)

0.50 g (3.3 mmol) 2-amino-N-hydroxy-benzamide and 0.49 g (3.3 mmol) phthalaldehydic acid are mixed with 5 ml ethoxyethanol and heated under stirring at 130° C. for 4 h. After cooling to room temperature 5 ml water are added, the white precipitate is filtered on a suction filter and washed twice with 5 ml water. The product is dried at 50° C. under vacuum overnight. Yield 0.65 g (75% of theory), white crystals, mp. 185° C.

1H-NMR ([ppm], DMSO-d6): 6.60 (s, 1 H, CH), 7.35-8.10 (m, 8 H, arom. H), 10.3 (s, 1 H, OH)
LC/MS (ACPI pos. mode): [M+1]=267.

EXAMPLE 14

Preparation of Compound (114)

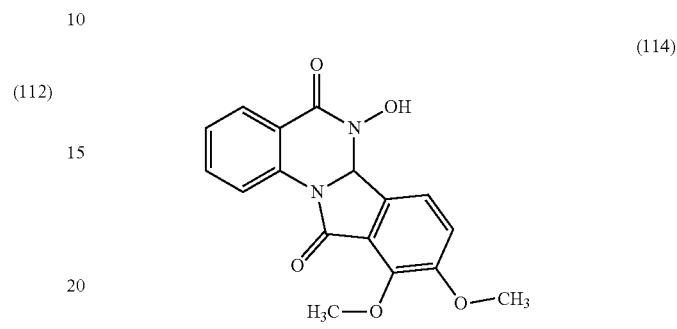
(114)

Analogous to example 13 is prepared compound (114) by reaction of 0.50 g (3.3 mmol) 2-amino-N-hydroxy-benzamide and 0.69 g (3.3 mmol) 6-formyl-2,3-dimethoxy-benzoic acid. Yield 1.07 g (100% of theory), mp. 240° C.
1H-NMR ([ppm], DMSO-d6): 3.30 (s, 6H, CH$_3$), 6.42 (s, 1H, CH), 7.35-8.05 (m, 6H, arom. H), 10.22 (s, 1H, OH)
LC/MS (ACPI pos. mode): [M+1]=327.

EXAMPLE 15

Preparation of Compound (115)

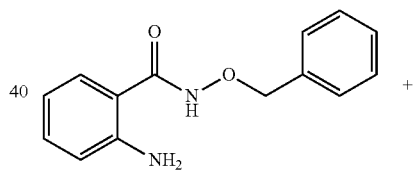

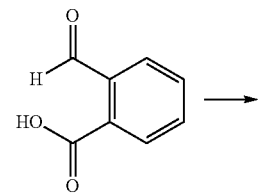

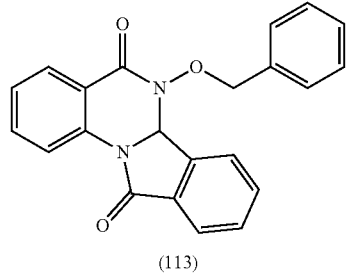
(113)

0.60 g (2.5 mmol) 2-amino-N-benzyloxy-benzamide and 0.37 g (2.0 mmol) phthalaldehydic acid are mixed with 6 ml ethoxyethanol and heated under stirring at 130° C. for 4 h. After cooling to room temperature the solvent is evaporated, the viscous residue is triturated with water and the white precipitate is filtered on a suction filter and washed twice with 5 ml methanol. The product is dried at 50° C. under vacuum overnight. Yield 0.58 g (64% of theory), white crystals, mp. 189° C.

1H-NMR ([ppm], CDCl3): 4.55 (d, 1 H, CH), 5.15 (d, 1 H, CH), 6.25 (s, 1 H, NCH), 7.30-8.20 (m, 13 H, arom. H).

LC/MS (ACPI pos. mode): [M+1]=357

EXAMPLE 16

Preparation of Compound (116)

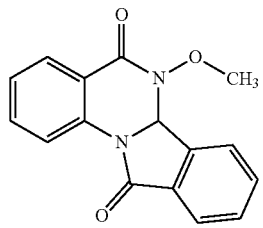

(116)

Analogous to example 16 is prepared compound (116) by reaction of 1.8 g (10.0 mmol) 2-amino-N-methoxy-benzamide and 1.50 g (10.0 mmol) phthalaldehydic acid. Yield 1.35 g (50% of theory), mp. 164° C.

1H-NMR ([ppm], CDCl3): 3.75 (s, 3H, CH$_3$), 6.22 (s, 1H, CH), 7.32-8.20 (m, 8H, arom. H).

LC/MS (ACPI pos. mode): [M+1]=281

EXAMPLE 17

Stabilization of Polypropylene

Method 1:

The employed mini-extruder, which is commercially available from DSM, enables a flow of the melted polymer in a circle, i.e. two screws in a twin-screw arrangement press the melted polymer to the outlet, which is connected to the inlet zone of the extruder. The temperature of the steel barrel of the mini-extruder can be regulated and the inlet zone of the extruder can be purged with a gas, which allows the removal of entrapped air originating from the loading of the polymer sample. Furthermore, a sensor determines the force, which is exerted by the melted polymer onto the barrel during rotation of the two screws. A change in the viscosity of the melted polymer leads to a change of the force.

The steel housing of the extruder is set at a temperature of 280° C. and the inlet zone is set under a nitrogen flow of 20 mL/min. At a screw speed of 50 rpm, 9 g of a mixture, which consists of 8.955 g of a pipe grade polypropylene random copolymer (d=0.905 g/cm$^3$, melt flow index 0.25 g/10 min (230° C./2.16 kg), melting point 142° C. (measured by DSC with a heating rate of 10 K/min; 99.95% of the overall mixture) and 0.0045 g of a compound according to the invention (0.05% of the overall mixture) are loaded. In case of the comparative example 17a), no compound according to the invention is added. Said polypropylene random copolymer itself already contains 0.2% tetrakis-[3-(3,5-di-tert-butyl-4-hydroxy-phenyl)-propionyloxymethyl]-methane, 0.2% 1,3,5-tri-(2,6-tert-butyl-4-hydroxybenzyl)-2,4,6-trimethylbenzene, 0.1% tris-(2,4-di-tert-butylphenyl)phosphite and 0.05% calcium stearate.

Tetrakis-[3-(3,5-di-tert-butyl-4-hydroxy-phenyl)-propionyloxymethyl]methane is a phenolic antioxidant, which is contained for example in Irganox 1010 (RTM BASF), as depicted:

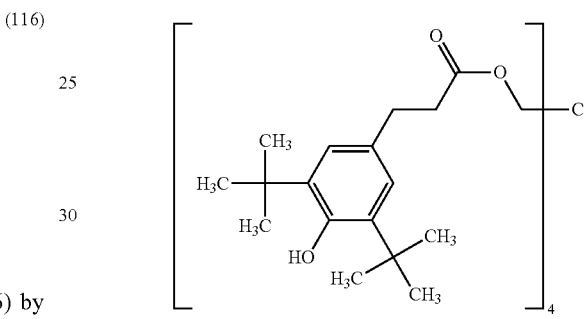

1,3,5-Tri-(2,6-tert-butyl-4-hydroxybenzyl)-2,4,6-trimethylbenzene is a phenolic antioxidant, which is contained for example in Irganox 1330 (RTM BASF), as depicted:

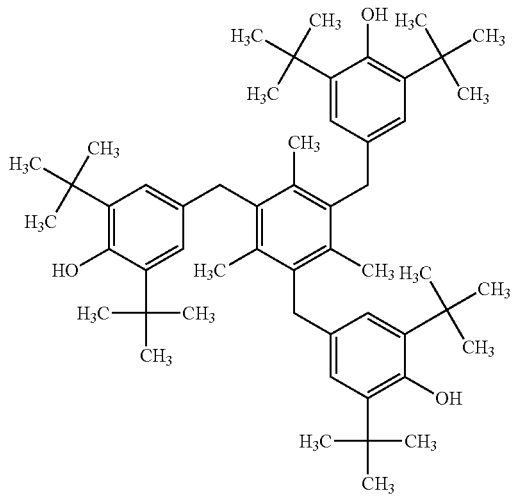 [SMILES: Cc1c(Cc2cc(C(C)(C)C)c(O)c(C(C)(C)C)c2)c(C)c(Cc2cc(C(C)(C)C)c(O)c(C(C)(C)C)c2)c(C)c1Cc1cc(C(C)(C)C)c(O)c(C(C)(C)C)c1]

Tris-(2,4-di-tert-butylphenyl)phosphite is a phosphite stabilizer, which is contained for example in Irgafos 168 (RTM BASF), as depicted:

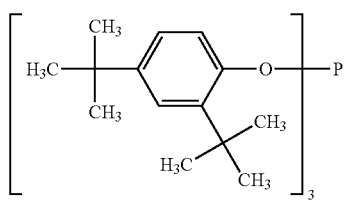

After loading, the screw speed is set to 100 rpm and the force exerted on the barrel is recorded. The test is conducted for 10 min under nitrogen at a flow rate of 20 mL/min. After a short period, a steady decrease of the force is recorded. The decrease of the force is quantified as slope of the force-to-time curve, wherein the slope is calculated between the time period of 7 and 10 minutes. The curve is rather linear during said period. The decrease of the force with time is taken as degree of melt-degradation of the polymer sample.

Desired is a minimum of degradation, which is expressed by a small value for the slope of the curve. No degradation would mean zero slope. The results are shown in table 1.

TABLE 1

| Example | Tested composition | Method 1 [slope] |
|---|---|---|
| 17a) [a] | without addition of a compound according to the invention | −0.70 |
| | with compound | |
| 17b) [b] | (101) | −0.20 |
| 17c) [b] | (102) | −0.15 |
| 17d) [b] | (103) | −0.15 |
| 17e) [b] | (104) | −0.20 |
| 17f) [b] | (105) | −0.26 |
| 17g) [b] | (106) | −0.27 |
| 17h) [b] | (107) | −0.33 |
| 17i) [b] | (108) | −0.34 |
| 17j) [b] | (109) | −0.40 |
| 17k) [b] | (110) | −0.44 |
| 17l) [b] | (111) | −0.44 |
| 17m) [b] | (113) | −0.44 |
| 17n) [b] | (114) | −0.41 |

[a] comparative
[b] according to the invention

EXAMPLE 18

Stabilization of Polypropylene

Method 2:
2500 g of polypropylene random copolymer (as described in example 17 under method 1 and including the mentioned additives) is blended with 1.25 g of a compound according to the invention and compounded under nitrogen at 220° C. with a twin screw extruder. In case of the comparative example 18a), no compound according to the invention is added. The pellets are extruded 5 more times at 280° C. under air. The melt flow of the pellets after the 5th extrusion is measured at 230° C. with a weight of 5 kg according to ISO 1133:1997.

A very small change of the melt index indicates less degradation. Ideally, there would be no change in melt flow. The results are shown in table 2.

TABLE 2

| Example | Tested composition | Method 2 [melt flow (5 kg/230° C.) after 5th extrusion in g/10 min] |
|---|---|---|
| 18a) [a] | without addition of a compound according to the invention | 3.35 |
| | with compound | |
| 18b) [b] | (101) | 2.3 |

Footnotes are listed at table 1.

EXAMPLE 19

Stabilization of Polypropylene

Method 3:
2500 g of polypropylene homopolymer (based on Moplen HF500N [RTM LyondellBasell] with MFI=12 dg/min, but containing additionally 0.05% calcium stearate, 0.04% Irganox 1010, and 0.04% Irgafos 168) is blended with 1.25 g of a compound according to the invention and compounded under nitrogen at 220° C. with a twin screw extruder. In case of the comparative example 19a), no compound according to the invention is added. The pellets are extruded 5 more times at 280° C. under air. The melt flow of the pellets after the 5th extrusion is measured at 230° C. with a weight of 2.16 kg according to ISO 1133: 1997.

A very small change of the melt index indicates less degradation. Ideally, there would be no change in melt flow. The results are shown in table 3.

TABLE 3

| Example | Tested composition | Method 3 [melt flow (2.16 kg/230° C.) after 5th extrusion in g/10 min] |
|---|---|---|
| 19a) [a] | without addition of a compound according to the invention | 48 |
| | with compound | |
| 19b) [b] | (101) | 23 |

Footnotes are listed at table 1.

EXAMPLE 20

Stabilization of Polypropylene 2 kg Moplen HF501N (RTM LyondellBasell, polypropylene homopolymer with MFI=10 dg/min, commercial product of LyondelBasell) is mixed with 0.05% calcium stearate, 0.033% Irganox 1010 and the additives listed in table 4. The resulting powder is compounded under nitrogen blanket at 200° C. on a single screw extruder. The composition is then extruded 5 times at 260° C. under air and samples are taken after the first, third and fifth extrusion pass. The melt flow index (=MFI) of the samples is measured according to ISO 1133:1997 and depicted in table 4.

TABLE 4

| composition | compound (101) | Irgafos 168 [c] | MFI (2.16 kg/230° C.) in g/10 min | | |
|---|---|---|---|---|---|
| | | | 1st pass | 3rd pass | 5th pass |
| 1 [a] | — | 0.067% | 11.3 | 16.0 | 22.4 |
| 2 [b] | 0.011% | 0.026% | 11.0 | 14.7 | 20.0 |

Footnotes [a] and [b] are listed at table 1.
[c] phosphite stabilizer described at example 17

The results of table 4 indicate that composition 2 provides a better melt stability than composition 1 despite of the replacement of 0.041% Irgafos 168 with only 0.011% of compound (101).

EXAMPLE 21

Stabilization of Polypropylene 2 kg Moplen HF500N (RTM LyondellBassell, polypropylene homopolymer with MFI=10 dg/min) is mixed with 0.05% calcium stearate, 0.033% Irganox 1010 and the additives listed in table 5. The resulting powder is compounded under nitrogen blanket at 200° C. on a single screw extruder. The compounded composition is then extruded 5 times at 260° C. under air and samples are taken initially and after the first, third and fifth extrusion pass. The melt flow index (=MFI) according to ISO 1133:1997 and the yellowness index (=YI) according to ASTM D1925 75 (C/2) of the samples are measured and depicted in table 5. Furthermore, a 2 mm tensile bar 5A is generated by injection-molding at 240° C. and this initial sample is put in an oven at 135° C. and visually inspected twice a week. The time to first signs of degradation (chalking) is monitored and depicted in table 5.

TABLE 5

| composition | 1 [a] | 2 [a] | 3 [a] | 4 [a] | 5 [b] | 6 [b] |
|---|---|---|---|---|---|---|
| Irgafos 168 [c] | 0.077% | 0.067% | 0.037% | 0.026% | 0.030% | 0.026% |
| compound (101) | — | — | — | — | 0.007% | 0.011% |
| MFI (2.16 kg/230° C.) in g/10 min | | | | | | |
| initially | — | 11.1 | 12.2 | — | 12.6 | 14 |
| 1st pass | — | 15.7 | 17.5 | — | 15.9 | 15.2 |
| 3rd pass | — | 19.3 | 27.1 | — | 19.8 | 20.4 |
| 5th pass | — | 26.5 | 32.2 | — | 26.4 | 25.2 |
| YI | | | | | | |
| initially | — | 0.3 | 0.3 | — | 0.2 | 0.1 |
| 1st pass | — | 1.3 | 1.3 | — | 0.3 | 0 |
| 3rd pass | — | 2.6 | 3.1 | — | 1.3 | 1.8 |
| 5th pass | — | 4.5 | 3.6 | — | 2.9 | 2.8 |
| Long term thermal stability 135° C. in days to embrittlement | 75 | 68 | 75 | 58 | 68 | 68 |

Footnotes are listed at table 4.

The MFI results indicate that composition 5, where 0.037% Irgafos 168 is replaced with only 0.007% compound (101), has a similar melt stability as the reference composition 2. Additionally, it is observed that the compositions 5 and 6 containing both compound (101) show slightly less discoloration (YI 2.9 and 2.8) than the reference compositions 2 and 3 (YI 4.5 and 3.6). The oven aging results indicate that compound (101) does not influence the thermal stability of the samples.

EXAMPLE 22

Stabilization of Polyethylene

Polyethylene MG9641 (an unstabilized PE-HD grade of Borealis in powder form) is compounded with the additives as listed in table 6 on a single screw extruder at 180° C. under nitrogen blanked. The composition is then extruded 5 times at 260° C. under air and samples are taken after the first, third and fifth extrusion pass. The melt flow index (=MFI) of the samples is measured according to ISO 1133:1997.

This polymer type tends to increase molecular mass during processing due to branching. Hence, higher MFIs indicate less branching, which means better melt stability during extrusion. The results are depicted in table 6.

TABLE 6

| composition | 1 [a] | 2 [b] |
|---|---|---|
| Irganox 1010 [d] | — | 0.05% |
| Irgafos 168 [c] | — | 0.02% |
| compound (101) | — | 0.02% |
| MFI (2.16 kg/190° C.) in g/10 min | | |
| 1st pass | 7.50 | 7.40 |
| 3rd pass | 4.80 | 7.70 |
| 5th pass | 3.25 | 7.10 |
| MFI (5 kg/190° C.) in g/10 min | | |
| 1st pass | 21.4 | 23.0 |
| 3rd pass | 16.9 | 22.2 |
| 5th pass | 12.3 | 21.2 |

Footnotes [a], [b] and [c] are listed at table 4.
[d] phenolic antioxidant described at example 17

The small changes of the MFI values at composition 2 containing compound (101) indicate a good processing stability.

EXAMPLE 23

Stabilization of Polyethylene

Exxon LD100MED (RTM ExxonMobile Chemicals, an unstabilized PE-LD grade) is ground to powder and compounded with the additives as listed in table 7 on a single screw extruder at 180° C. under nitrogen blanked. The composition is then extruded 5 times at 260° C. under air and samples are taken after the first, third and fifth extrusion pass. The melt flow index (=MFI) of the samples is measured according to ISO 1133:1997.

This polymer type tends to increase molecular mass during processing due to branching. So higher MFIs indicate less branching, which means better melt stability during extrusion. The results are depicted in table 7.

TABLE 7

| composition | 1 [a)] | 2 [a)] | 3 [b)] |
|---|---|---|---|
| Irganox 1076 [e)] | 0.05% | 0.05% | 0.05% |
| Irgafos 38 [f)] | — | 0.05% | 0.02% |
| compound (101) | — | — | 0.01% |
| MFI (2.16 kg/190° C.) in g/10 min | | | |
| 1$^{st}$ pass | 2.10 | 2.25 | 2.20 |
| 3$^{rd}$ pass | 2.00 | 2.25 | 2.10 |
| 5$^{th}$ pass | 1.90 | 2.10 | 2.10 |

Footnotes [a)] and [b)] are listed at table 1.

[e)] Irganox 1076 [RTM BASF] contains as a phenolic antioxidant a component as depicted

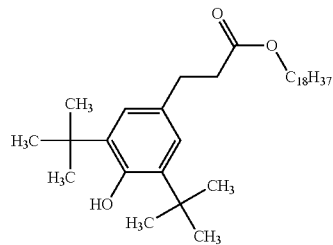

and for which one chemical name is stearyl β-(3,5-di-tert-butyl-4-hydroxyphenyl)-propionate

[f)] Irgafos 38 [RTM BASF] contains as a phosphite stabilizer a component as depicted

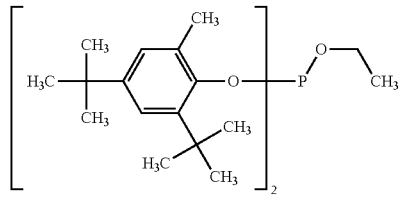

and for which one chemical name is bis-(2,4-di-tert-butyl-6-methyl-phenyl)-ethyl phosphite.

The MFI values of composition 2 and of composition 3 are very similar despite of replacement of 0.03% Irgafos 38 with only 0.01% component (101).

The invention claimed is:
1. A composition, which comprises
a) an organic material susceptible to oxidative, thermal or light-induced degradation, said material is one or more selected from the group consisting of a polymer, an oligohydroxy compound, a wax, a fat and a mineral oil, with the proviso that the polymer is not a polypeptide, agar-agar or a component of agar-agar and the oligohydroxy compound is not glucose or a component of agar-agar; and b) a compound of formula I

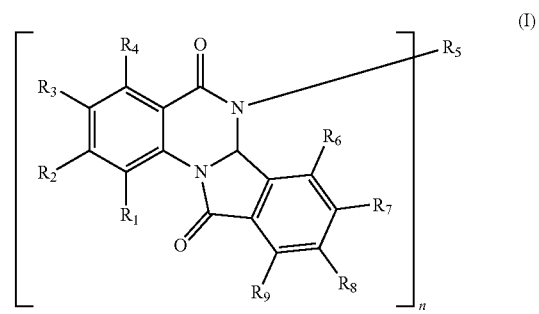

wherein
when n is 1,
$R_5$ is H, $C_1$-$C_{30}$-alkyl, $C_3$-$C_{10}$-cycloalkyl, $C_6$-$C_{10}$-aryl, which is unsubstituted or substituted by $C_1$-$C_8$-alkyl, $C_1$-$C_8$-alkoxy, halogen or one phenyl, $C_7$-$C_{13}$-aralkyl, $C_2$-$C_{22}$-alkenyl, $C_3$-$C_{12}$-alkinyl, OH, $C_1$-$C_{30}$-alkyloxy, $C_3$-$C_{10}$-cycloalkyloxy, $C_6$-$C_{12}$-aryloxy, $C_7$-$C_{13}$-aralkyloxy, hydroxy-$C_1$-$C_8$-alkyl, carboxy-$C_1$-$C_{12}$-alkyl, $C_1$-$C_{12}$-alkoxycarbonyl-$C_1$-$C_{12}$-alkyl, $C_2$-$C_{30}$-alkyl, which is interrupted by one or more oxygen atoms, $C_2$-$C_{16}$-alkyl, which is interrupted by one sulfur atom, or $NR'_1R'_2$;
when n is 2,
$R_5$ is $C_1$-$C_{12}$-alkane-diyl, $C_6$-$C_{14}$-arylene, $C_4$-$C_8$-cycloalkane-bis-($C_1$-$C_4$-alkylene), $C_6$-$C_{14}$-arene-bis-($C_1$-$C_4$-alkylene), $C_4$-$C_{24}$-alkane-diyl, which is interrupted by one or more oxygen atoms, $C_4$-$C_{20}$-alkane-diyl, which is interrupted by one or more —NH—, —N($C_1$-$C_8$-alkyl)- or —N(hydroxy-$C_1$-$C_8$-alkyl)-, piperazine-N,N'-bis-($C_1$-$C_4$-alkylene) or $C_2$-$C_{10}$-alkane-diyl, which is interrupted by one sulfur atom;
when n is 3,
$R_5$ is $C_5$-$C_{12}$-alkane-triyl, $C_5$-$C_{24}$-alkane-triyl, which is interrupted by one or more oxygen atoms, $C_5$-$C_{24}$-alkane-triyl, which is interrupted by one or more —NH—, —N($C_1$-$C_8$-alkyl)- or —N(hydroxy-$C_1$-$C_8$-alkyl)-;
when n is 4,
$R_5$ is $C_5$-$C_{24}$-alkane-tetrayl, $C_6$-$C_{24}$-alkane-tetrayl, which is interrupted by one or more oxygen atoms, or $C_6$-$C_{24}$-alkane-tetrayl, which is interrupted by one or more —NH—, —N($C_1$-$C_8$-alkyl)- or —N(hydroxy-$C_1$-$C_8$-alkyl)-;
n is 1, 2, 3 or 4;
$R_1$ to $R_4$ and $R_6$ to $R_9$ are each independently from each other H, $C_1$-$C_{12}$-alkyl, $C_3$-$C_{10}$-cycloalkyl, $C_3$-$C_{22}$-alkenyl, $C_1$-$C_{12}$-alkoxy, $C_1$-$C_{12}$-alkylsulfanyl, hydroxy-$C_1$-$C_8$-alkyl, halogen, $NR''_1R''_2$, $NO_2$, CN, phenyl, phenyloxy or $R_1$ and $R_2$ or $R_2$ and $R_3$ or $R_3$ and $R_4$ or $R_6$ and $R_7$ or $R_7$ and $R_8$ or $R_8$ and $R_9$ are linked together to form a five- or 6-membered alicylic, aromatic or heterocyclic ring together with their 2 corresponding carbons atoms, to which they are attached; and
$R'_1$, $R'_2$, $R''_1$ and $R''_2$ are each independently from each other H, $C_1$-$C_{12}$-alkyl, $C_3$-$C_{10}$-cycloalkyl, hydroxy-$C_1$-$C_8$-alkyl, $C_3$-$C_{22}$-alkenyl, $C_6$-$C_{10}$-aryl, which is unsubstituted or substituted by $C_1$-$C_8$-alkyl, $C_1$-$C_8$-alkoxy, halogen or one phenyl, $C_7$-$C_{12}$-aralkyl, carboxy-$C_1$-$C_{12}$-alkyl, $C_1$-$C_{12}$-alkoxycarbonyl-$C_1$-$C_{12}$-alkyl, or carboxy-$C_6$-$C_{10}$-aryl, or $R'_1$ and $R'_2$ or $R''_1$ and $R''_2$ form together with the nitrogen atom, to which they are attached, a 5- or 6-membered alicyclic, aromatic or heterocyclic ring.

2. The composition according to claim 1, wherein the organic material is a polyolefin or a copolymer thereof, a polystyrene or a copolymer thereof, a polyurethane or a copolymer thereof, a polyether, which is obtainable by the polycondensation of an expoxide, an oxetane or tetrahydrofuran, or a copolymer thereof, a polyol, a polyester or a copolymer thereof, a polycarbonate or a copolymer thereof, a polyvinyl chloride or a copolymer thereof, a polyvinylidene chloride or a copolymer thereof, a polysulfone or a copolymer thereof, a polybutadiene or a copolymer thereof, a polyvinylacetate or a copolymer thereof, a polyvinylalcohol or a copolymer thereof, polyvinylacetale or a copolymer thereof, a polyamide, which is obtainable by polycondensation of a diamine and a dicarboxylic acid, or a copolymer thereof, a polyamide, which is obtainable by polycondensation of $H_2N-(CH_2)_x-CH_2-COOH$ with x=1 to 10, or a copolymer thereof, an oligohydroxy compound, a wax, a fat or a mineral oil.

3. The composition according to claim 1, wherein in formula I when n is 1, $R_5$ is H, $C_1$-$C_{30}$-alkyl, $C_3$-$C_{10}$-cycloalkyl, $C_6$-$C_{10}$-aryl, which is unsubstituted or substituted by $C_1$-$C_8$-alkyl, $C_1$-$C_8$-alkoxy, halogen or one phenyl, $C_7$-$C_{13}$-aralkyl, $C_2$-$C_{22}$-alkenyl, $C_3$-$C_{12}$-alkinyl, OH, $C_1$-$C_{30}$-alkyloxy, $C_3$-$C_{10}$-cycloalkyloxy, $C_6$-$C_{12}$-aryloxy, $C_7$-$C_{13}$-aralkyloxy, hydroxy-$C_1$-$C_8$-alkyl, carboxy-$C_1$-$C_{12}$-alkyl, $C_1$-$C_{12}$-alkoxycarbonyl-$C_1$-$C_{12}$-alkyl, $C_2$-$C_{30}$-alkyl, which is interrupted by one or more oxygen atoms, $C_2$-$C_{16}$-alkyl, which is interrupted by one sulfur atom, or $NR'_1R'_2$;

when n is 2, $R_5$ is $C_1$-$C_{12}$-alkane-diyl, $C_6$-$C_{14}$-arylene, $C_4$-$C_8$-cycloalkane-bis-($C_1$-$C_4$-alkylene), $C_6$-$C_{14}$-arene-bis-($C_1$-$C_4$-alkylene), $C_4$-$C_{24}$-alkane-diyl, which is interrupted by one or more oxygen atoms, $C_4$-$C_{20}$-alkane-diyl, which is interrupted by one or more —NH—, —N($C_1$-$C_8$-alkyl)- or —N(hydroxy-$C_1$-$C_8$-alkyl)-, piperazine-N.N'-bis-($C_1$-$C_4$-alkylene) or $C_2$-$C_{10}$-alkane-diyl, which is interrupted by one sulfur atom;

n is 1 or 2;

$R_1$ to $R_4$ and $R_6$ to $R_9$ are each independently from each other H, $C_1$-$C_{12}$-alkyl, $C_3$-$C_{10}$-cycloalkyl, $C_3$-$C_{22}$-alkenyl, $C_1$-$C_{12}$-alkoxy, $C_1$-$C_{12}$-alkylsulfanyl, hydroxy-$C_1$-$C_8$-alkyl, halogen, $NR''_1R''_2$, $NO_2$, CN, phenyl, phenyloxy or $R_1$ and $R_2$ or $R_2$ and $R_3$ or $R_3$ and $R_4$ or $R_6$ and $R_7$ or $R_7$ and $R_8$ or $R_8$ and $R_9$ are linked together to form a five- or 6-membered alicylic, aromatic or heterocyclic ring together with their 2 corresponding carbons atoms; and $R'_1$, $R'_2$, $R''_1$ and $R''_2$ are each independently from each other H, $C_1$-$C_{12}$-alkyl, $C_3$-$C_{10}$-cycloalkyl, hydroxy-$C_1$-$C_8$-alkyl, $C_3$-$C_{22}$-alkenyl, $C_6$-$C_{10}$-aryl, which is unsubstituted or substituted by $C_1$-$C_8$-alkyl, $C_1$-$C_8$-alkoxy, halogen or one phenyl, $C_7$-$C_{12}$-aralkyl, carboxy-$C_1$-$C_{12}$-alkyl, $C_1$-$C_{12}$-alkoxycarbonyl-$C_1$-$C_{12}$-alkyl, or carboxy-$C_6$-$C_{10}$-aryl, or $R'_1$ and $R'_2$ or $R''_1$ and $R''_2$ form together with the nitrogen atom, to which they are attached, a 5- or 6-membered alicyclic, aromatic or heterocyclic ring.

4. The composition according to claim 1, wherein in formula I when n is 1, $R_5$ is H, $C_1$-$C_{30}$-alkyl, $C_3$-$C_{10}$-cycloalkyl, $C_6$-$C_{10}$-aryl, which is unsubstituted or substituted by $C_1$-$C_8$-alkyl, $C_1$-$C_5$alkoxy, halogen or one phenyl, $C_7$-$C_{13}$-aralkyl, $C_2$-$C_{22}$-alkenyl, $C_3$-$C_{12}$-alkinyl, OH, $C_1$-$C_{30}$-alkyloxy, $C_3$-$C_{10}$-cycloalkyloxy, $C_6$-$C_{12}$-aryloxy, $C_7$-$C_{13}$-aralkyloxy, hydroxy-$C_1$-$C_8$-alkyl, carboxy-$C_1$-$C_{12}$-alkyl, $C_1$-$C_{12}$-alkoxycarbonyl-$C_1$-$C_{12}$-alkyl, $C_2$-$C_{30}$-alkyl, which is interrupted by one or more oxygen atoms, $C_2$-$C_{16}$-alkyl, which is interrupted by one sulfur atom, or $NR'_1R'_2$;

when n is 2, $R_5$ is $C_1$-$C_{12}$-alkane-diyl, $C_4$-$C_{24}$-alkane-diyl, which is interrupted by one or more oxygen atoms, $C_4$-$C_{20}$-alkane-diyl, which is interrupted by one or more —NH—, —N($C_1$-$C_8$-alkyl)- or —N(hydroxy-$C_1$-$C_8$-alkyl)-, piperazine-N,N'-bis-($C_1$-$C_4$-alkylene) or $C_2$-$C_{10}$-alkane-diyl, which is interrupted by one sulfur atom;

n is 1 or 2;

2 substituents out of $R_1$ to $R_4$ and 2 substituents out of $R_6$ to $R_9$ are H and the other remaining 4 substituents out of $R_1$ to $R_4$ and $R_6$ to $R_9$ are each independently from each other H, $C_1$-$C_{12}$-alkyl, $C_3$-$C_{10}$-cycloalkyl, $C_3$-$C_{22}$-alkenyl, $C_1$-$C_{12}$-alkoxy, $C_1$-$C_{12}$-alkylsulfanyl, hydroxy-$C_1$-$C_8$-alkyl, halogen, $NR''_1R''_2$, $NO_2$, CN, phenyl, phenyloxy; and $R'_1$, $R'_2$, $R''_1$ and $R''_2$ are each independently from each other H, $C_1$-$C_{12}$-alkyl, $C_3$-$C_{10}$-cycloalkyl, hydroxy-$C_1$-$C_8$-alkyl, $C_3$-$C_{22}$-alkenyl, $C_6$-$C_{10}$-aryl, which is unsubstituted or substituted by $C_1$-$C_8$-alkyl, $C_1$-$C_8$-alkoxy, halogen or one phenyl, $C_7$-$C_{12}$-aralkyl, carboxy-$C_1$-$C_{12}$-alkyl, $C_1$-$C_{12}$-alkoxycarbonyl-$C_1$-$C_{12}$-alkyl, or carboxy-$C_6$-$C_{10}$-aryl, or $R'_1$ and $R'_2$ or $R''_1$ and $R''_2$ form together with the nitrogen atom, to which they are attached, a pyrrolidine, a piperidine or a morpholine ring.

5. The composition according to claim 1, wherein in formula I n is 1, $R_5$ is H, $C_1$-$C_{30}$-alkyl, $C_3$-$C_{10}$-cycloalkyl, $C_6$-$C_{10}$-aryl, which is unsubstituted or substituted by $C_1$-$C_8$-alkyl or $C_1$-$C_8$-alkoxy, $C_7$-$C_{13}$-aralkyl, $C_2$-$C_{22}$-alkenyl, OH, $C_1$-$C_{30}$-alkyloxy, $C_3$-$C_{10}$-cycloalkyloxy, $C_6$-$C_{12}$-aryloxy, $C_7$-$C_{13}$-aralkyloxy, hydroxy-$C_1$-$C_8$-alkyl, carboxy-$C_1$-$C_{12}$-alkyl, $C_1$-$C_{12}$-alkoxycarbonyl-$C_1$-$C_{12}$-alkyl, $C_2$-$C_{30}$-alkyl, which is interrupted by one or more oxygen atoms, or $NR'_1R'_2$;

3 substituents out of $R_1$ to $R_4$ and 2 substituents out of $R_6$ to $R_9$ are H and the other remaining 3 substituents out of $R_1$ to $R_4$ and $R_6$ to $R_9$ are each independently from each other H, $C_1$-$C_{12}$-alkyl, $C_1$-$C_{12}$-alkoxy or halogen; and $R'_1$ and $R'_2$ are each independently from each other H, $C_1$-$C_{12}$-alkyl, $C_3$-$C_{10}$-cycloalkyl, $C_3$-$C_{22}$-alkenyl, $C_6$-$C_{10}$-aryl, which is unsubstituted or substituted by $C_1$-$C_8$-alkyl or $C_1$-$C_8$-alkoxy, $C_7$-$C_{12}$-aralkyl, or $R'_1$ and $R'_2$ form together with the nitrogen atom, to which they are attached, a pyrrolidine, a piperidine or a morpholine ring.

6. The composition according to claim 1, wherein the organic material is a polymer, and said polymer is a polyolefin or a copolymer thereof, a polystyrene or a copolymer thereof, or a polyurethane or a copolymer thereof.

7. The composition according to claim 1, wherein component b) is contained in an amount of 0.0005% to 10% based on the weight of component a).

8. The composition according to claim 1, further comprising an additive component c).

9. The composition according to claim 8, wherein component c) comprises a phosphite or phosphonite, an acid scavenger, a phenolic antioxidant or an aminic antioxidant.

10. The composition according to claim 8 wherein component c) is a phenolic antioxidant, a phosphite or phosphonite.

11. The composition according to claim 8, wherein component c) is tetrakis-[β-(3,5-di-tert-butyl-4-hydroxyphenyl)-propionyloxymethyl]methane or stearyl β-(3,5-di-tert-butyl-4-hydroxyphenyl)-propionate.

12. The composition according to claim 8, wherein component c) is tris-(2,4-di-tert-butyl)phosphite.

13. The composition according to claim 8, wherein the weight ratio of component b) to component c) is from 4:1 to 1:20, and the combined amount of component b) and component c) is below 80% based on the weight of component a).

14. The composition according to claim 8 further comprising component d), a second additive, which is a phosphite or phosphonite, an acid scavenger, a phenolic antioxidant or an aminic antioxidant, with the proviso that component d) is different than component c).

15. The composition according to claim 14 wherein
c) is a phenolic antioxidant, and
d) is a phosphite or phosphonite.

16. The composition according to claim 15, wherein component c) is tetrakis-[β-(3,5-di-tert-butyl-4-hydroxyphenyl)-propionyloxymethyl]methane or stearyl β-(3,5-di-tert-butyl-4-hydroxyphenyl)-propionate.

17. The composition according to claim 15, wherein component d) is tris-(2,4-di-tert-butyl)phosphite.

18. The composition according to claim 15, wherein component c) is tetrakis-[β-(3,5-di-tert-butyl-4-hydroxyphenyl)-propionyloxymethyl]methane or stearyl β-(3,5-di-tert-butyl-4-hydroxyphenyl)-propionate, and component d) is tris-(2,4-di-tert-butyl)phosphite.

19. A method for protection of an organic material susceptible to oxidative, thermal or light-induced degradation as defined in claim 1, said method comprising
incorporating into or applying onto said organic material a compound of formula I.

20. The method according to claim 19, wherein the organic material is a polymer, and incorporation of the compound of formula I into the organic material is accomplished in part or entirely at a temperature between 135° C. to 350° C.

21. A compound of formula I

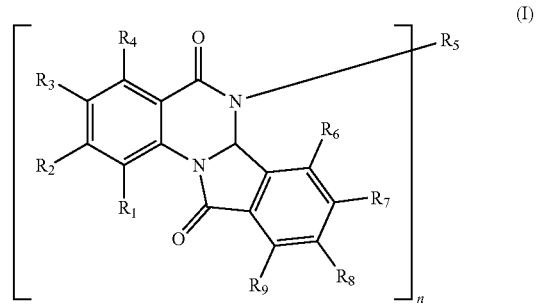

wherein
n is 1,
$R_5$ is $C_1$-$C_{30}$-alkyloxy, $C_3$-$C_{10}$-cycloalkyloxy, $C_6$-$C_{12}$-aryloxy, $C_7$-$C_{13}$-aralkyloxy or $NR'_1R'_2$;
3 substituents out of $R_1$ to $R_4$ and 2 substituents out of $R_6$ to $R_9$ are H and the other remaining 3 substituents out of $R_1$ to $R_4$ and $R_6$ to $R_9$ are each independently from each other H, $C_1$-$C_{12}$-alkoxy or halogen; and
$R'_1$ and $R'_2$ are each independently from each other H, $C_1$-$C_{12}$-alkyl, $C_3$-$C_{10}$-cycloalkyl, $C_3$-$C_{22}$-alkenyl, $C_6$-$C_{10}$-aryl, $C_7$-$C_{12}$-aralkyl, or $R'_1$ and $R'_2$ form together with the nitrogen atom, to which they are attached, a pyrrolidine, a piperidine or a morpholine ring,
with the proviso that $R'_1$ and $R'_2$ are not both $C_1$-alkyl.

22. An additive composition, which comprises
b) the compound of formula I of claim 1, and
c) a further additive selected from a phosphite, a phosphonite, an acid scavenger, a phenolic antioxidant, an aminic antioxidant, or a mixture thereof.

23. The additive composition according to claim 22, wherein component c) is a phenolic antioxidant, a phosphite, or a phosphonite.

24. The additive composition according to claim 22, wherein component c) is tetrakis-[β-(3,5-di-tert-butyl-4-hydroxyphenyl)-propionyloxymethyl]methane, stearyl β-(3,5-di-tert-butyl-4-hydroxyphenyl)-propionate or tris-(2,4-di-tert-butyl)phosphite.

25. The additive composition according to claim 22 wherein
c) is a phenolic antioxidant, and further comprising
d) a second additive, which is a phosphite or phosphonite.

26. The additive composition according to claim 25, wherein component c) is tetrakis-[β-(3,5-di-tert-butyl-4-hydroxyphenyl)-propionyloxymethyl]methane or stearyl β-(3,5-di-tert-butyl-4-hydroxyphenyl)-propionate.

27. The additive composition according to claim 25, wherein component d) is tris-(2,4-di-tert-butyl)phosphite.

28. The additive composition according to claim 25, wherein component c) is tetrakis-[β-(3,5-di-tert-butyl-4-hydroxyphenyl)-propionyloxymethyl]methane or stearylβ-(3,5-di-tert-butyl-4-hydroxyphenyl)-propionate and component d) is tris-(2,4-di-tert-butyl)phosphite.

* * * * *